(12) United States Patent
Shang et al.

(10) Patent No.: US 12,719,229 B2
(45) Date of Patent: Aug. 25, 2026

(54) MULTIPLE FREQUENCY LASER SYSTEM FOR TREATING SKIN CONDITIONS

(71) Applicant: Candela Corporation, Marlborough, MA (US)

(72) Inventors: Xiaoming Shang, Lexington, MA (US); Zhi Huang, Boston, MA (US); Yimin Zang, Marlborough, MA (US); Kevin Schomacker, Maynard, MA (US)

(73) Assignee: CANDELA CORPORATION, Marlborough, MA (US)

( * ) Notice: Subject to any disclaimer, the term of this patent is extended or adjusted under 35 U.S.C. 154(b) by 299 days.

(21) Appl. No.: 18/627,533

(22) Filed: Apr. 5, 2024

(65) Prior Publication Data

US 2024/0347999 A1 Oct. 17, 2024

Related U.S. Application Data

(60) Provisional application No. 63/495,674, filed on Apr. 12, 2023.

(51) Int. Cl.
*H01S 3/094* (2006.01)
*A61N 5/06* (2006.01)
(Continued)

(52) U.S. Cl.
CPC ...... *H01S 3/094061* (2013.01); *A61N 5/0616* (2013.01); *A61N 5/067* (2021.08);
(Continued)

(58) Field of Classification Search
CPC ............. H01S 3/094061; H01S 3/0092; H01S 3/08081; H01S 3/094076; H01S 3/1024;
(Continued)

(56) References Cited

U.S. PATENT DOCUMENTS 7,792,162 B2 9/2010 Piper et al.
7,961,772 B2 6/2011 Tidemand-Lichtenberg et al.
(Continued)

FOREIGN PATENT DOCUMENTS

CN 203235152 U 10/2013
CN 203777519 U 8/2014

OTHER PUBLICATIONS

Written Opinion of International Application No. PCT/US2024/023292 received from the International Searching Authority dated Aug. 20, 2024, (5 pages).
(Continued)

*Primary Examiner* — John R Downey
(74) *Attorney, Agent, or Firm* — Iandiorio Teska & Coleman, LLP

(57) ABSTRACT

A multiple frequency laser system and method for treating skin conditions via a handpiece features a pump laser module having a single laser beam at a first frequency. A dual laser module receives the laser beam at the first frequency and includes dual free running laser resonators to produce a laser beam at a second frequency and a laser beam at a third frequency. A frequency conversion module receives as inputs the laser beam at the second frequency and the laser beam at the third frequency and is configured to selectively provide laser beams to the handpiece including a second harmonic generation of the second frequency, a second harmonic generation of the third frequency, a summed frequency generation of the second frequency and the third frequency, the laser beam at the first frequency, the laser beam at the second frequency, and/or the laser beam at the first frequency combined with the laser beam at the second frequency. The handpiece receives the laser beams from the frequency module and delivers them to skin for treatment.

31 Claims, 18 Drawing Sheets

(51) Int. Cl.

| | |
|---|---|
| ***A61N 5/067*** | (2006.01) |
| ***G02F 1/35*** | (2006.01) |
| ***G02F 1/37*** | (2006.01) |
| ***H01S 3/00*** | (2006.01) |
| ***H01S 3/08*** | (2023.01) |
| ***H01S 3/102*** | (2006.01) |
| ***H01S 3/16*** | (2006.01) |

(52) U.S. Cl.

CPC .............. *G02F 1/3534* (2013.01); *G02F 1/37* (2013.01); *H01S 3/0092* (2013.01); *H01S 3/08081* (2013.01); *H01S 3/094076* (2013.01); *H01S 3/1024* (2013.01); *H01S 3/1611* (2013.01); *A61N 2005/0659* (2013.01); *A61N 2005/0663* (2013.01)

(58) Field of Classification Search

CPC ..... H01S 3/1611; H01S 3/109; A61N 5/0616; A61N 5/067; A61N 2005/0659; A61N 2005/0663; A61N 2005/0626; G02F 1/3534; G02F 1/37; A61B 18/203; A61B 2018/20553; A61B 2018/2065

See application file for complete search history.

(56) References Cited

U.S. PATENT DOCUMENTS

| | | | |
|---|---|---|---|
| 8,320,418 | B2 | 11/2012 | Kuksenkov et al. |
| 9,709,873 | B2 | 7/2017 | Hansen et al. |
| RE46,937 | E | 7/2018 | Jensen et al. |
| 10,175,555 | B2 | 1/2019 | Chuang et al. |
| 2010/0002732 | A1 | 1/2010 | Tidemand-Lichtenberg |
| 2011/0306955 | A1 | 12/2011 | Thorhauge et al. |
| 2019/0159838 | A1* | 5/2019 | Boutoussov ........... A61B 18/20 |
| 2019/0336213 | A1* | 11/2019 | Rao ..................... H01S 3/10053 |
| 2021/0260401 | A1 | 8/2021 | Thorhauge et al. |
| 2022/0022961 | A1* | 1/2022 | Boutoussov ........... A61B 18/22 |

OTHER PUBLICATIONS

Lin et al., "Highly efficient LD-pumped 607 nm high-power CW Pr3+: YLF lasers", Optics and Laser Tech. 129 (2020) 106281.

S. Chen et al., "Orange, yellow and green emissions generated in Q-switched Nd:YALO3/YVO4 Raman laser", J. of Luminescence, 214, Oct. 2019, 116555.

Y. F. Chen et al., "Efficient high-power dual-wavelength lime-green Nd:YVO4 lasers", Optics Lett. 44, (2019), 1323.

Y. F. Chen et al., "High-power dual-color yellow-green solid-state self-Raman laser", Laser Physics, 29, (2019), 075802.

Y. C. Liu et al., Compact efficient high-power triple-color Nd:YVO4 yellow-lime-green self-Raman lasers, Optics Lett., 45, (2020), 1144.

S. Xie et al., A 7.5W quasi-continuous-wave sodium D2 laser generated from single-pass sum-frequency generation in LBO crystal, Appl Phys B, 102, (2011), 781.

P.F. Zhu et al., All Solid State Doubly Resonant Intracavity Frequency Sum Mixing Orange Yellow Laser with 3.2 W Output Power at 593.5 nm, Optics and Spectroscopy, 114(2013), 151.

Y.D. Zhao et. al., An efficient continuous-wave 591 nm light source based on sum-frequency mixing of a diode pumped Nd:GdVO4-Nd:CNGG laser, Laser Phys., 23, (2013), 85010.

Y. L. Li et al., Diode-pumped continuous wave self-sum frequency mixing yellow Nd:YAB laser at 592 nm, Laser Phys Lett., 8, (2011), 274.

J. Yang et al., Generation of a 578-nm Yellow Laser by the Use of Sum-Frequency Mixing in a Branched Cavity, IEEE Photonics J., 8, (2016), 1500607.

Q. Bian et al., High-power repetition rate- and pulse width-tunable 589 nm versatile laser for adaptive optical systems, Opt. Lett., 28, (2020), 13895.

N. Saito, et al., Development of all-solid-state coherent 589 nm light source: toward the realization of sodium lidar and laser guide star adaptive optics, Proc. Of SPIE, 6409, (2006), 64091H.

Z. Wang et al., Multiwavelength green-yellow laser based on a Nd:YAG laser with nonlinear frequency conversion in a LBO crystal, Appl. Opt., 51, (2012), 4196.

J. Zhang et al., A diode-pumped Nd:YAlO3 dual-wavelength yellow light source, Laser Phys., 23, (2013), 115001.

M. Li et al., Solid State Intracavity Sum Frequency Single Longitudinal Mode 593.5 nm Yellow Lasers, Chinese J. of Lasers, 47, (2020), 031003.

R.R. Anderson, Laser-tissue interaction in dermatology, In: Lasers in cutaneous and aesthetic surgery, K.A. Arndt (Ed.), pp. (26-51), Lippincott Williams and Wilkins, ISBN 0316051772, Boston, Massachusetts, USA.

* cited by examiner

MULTIPLE FREQUENCY LASER SYSTEM FOR TREATING SKIN CONDITIONS

RELATED APPLICATIONS

This application claims benefit of and priority to U.S. Provisional Application Ser. No. 63/495,674 filed Apr. 12, 2023, under 35 U.S.C. §§ 119, 120, 363, 365, and 37 C.F.R. § 1.55 and § 1.78, which is incorporated herein by this reference.

FIELD OF THE INVENTION

This subject invention relates to lasers used in dermatology.

BACKGROUND OF THE INVENTION

Lasers play an increasing role in treating various skin conditions including the clearance of vascular lesions, unwanted hair removal, pigmented lesions, and skin rejuvenation. The rapid acceptance of laser applications in dermatology has been largely facilitated by the theory of selective photothermolysis. This theory correlates the three laser parameters (i.e., wavelength, pulse duration, and fluence) to the size of the intended target to safely achieve the desired skin response. Specifically, proper laser wavelength needs to be chosen to selectively target the chromophore responsible for a particular skin condition. Some of the common chromophores in skin include hemoglobin (oxyhemoglobin and deoxyhemoglobin), melanosomal melanin, tattoo inks, water, fatty tissue, etc. Each chromophore manifests itself with unique absorption spectrum, as shown in FIG. 1. To effectively treat vascular related skin problems including hemangioma, port wine stain, rosacea, leg vein, etc., it is preferred to use a wavelength ranging from 500-600 nm to selectively target deoxyhemoglobin. Clinically, several wavelengths (i.e., 532 nm, 585 nm or 595 nm) are commonly used for vascular treatment with shorter wavelengths (i.e., 532 nm) for smaller and shallower vessels while the longer 585/595 nm for deeper and larger vessels. For even deeper blood vessels or dark skin patient, near infrared wavelength may be necessary. For example, 755 nm or 1064 nm have been proved to be effective to treat leg veins or patients with darker skin types. Therefore, multiple wavelengths from green, yellow, orange up to near infrared allowing are used for customized treatment leading to optimized clinical outcomes for different vascular lesions or different patient groups.

Removal of unwanted hair is another popular application of two near infrared wavelengths (i.e., 755 nm and 1064 nm). Furthermore, 755 nm may also be a good wavelength for pigmented lesions thanks to its well-balanced wavelength favoring absorption of melanosome over hemoglobin. In addition to vascular, hair, and pigmented treatment, lasers have been widely used for skin rejuvenation. For example, wrinkle reduction and skin tightening represent one of the fastest growing areas. Long pulsed lasers for skin tightening or wrinkle reduction mainly target water and rely on photothermal bulk heating resulting from substantial water absorption of the laser energy. The laser has to penetrate deep enough to reach dermis layer where the collagen is located. Heating collagen to temperatures between 65 and 80° C. leads to collagen contraction due to breaking hydrogen bonds reducing stain in the triple helix collagen fiber leading to immediate skin tightening or secondary stimulation of collagen growth via an inflammatory healing response in the skin occurring at lower temperatures. In this case, there are two requirements for laser wavelengths, i.e., sufficient water absorption and deep enough tissue penetration depth. As shown in FIG. 1, wavelength ranging from 1.2 um to 1.5 um may be proper for this purpose. Therefore, a laser system with multiple wavelength capability covering a broad range from visible wavelength to near infrared can offer optimized treatment of various skin conditions from vascular lesion, hair, pigmentation to skin tightening.

Based on the selective photothermolysis theory, the pulse duration needs to be shorter than the thermal relaxation time of a target chromophore present in the skin in order to selectively damage the target without causing unwanted thermal damage to the neighboring tissues. Depending on the target size for the blood vessel or hair follicle, the preferable pulse duration is estimated on the order of a few hundred microsecond to a few hundred milliseconds. To meet such clinical needs, a medical aesthetic laser should be designed in such a way that the pulse duration should be tunable over a large range from sub-millisecond to a hundred millisecond.

Another laser parameter is a high enough output energy to support sufficient fluence for effective treatment with large enough spot for the treatment of deep target as well as for fast treatment. For example, up to 15 $J/cm^2$ is typically needed to treat some vascular lesions. This translates to a delivered laser energy of more than 4 J for a spot size of 6 mm; 7 $J/cm^2$ in a 15 mm spot would require 12 J of laser energy delivered to tissue which is made even harder when 1 ms pulse durations are also needed translating to a peak power of 12 kW.

But, there is no known multi-joule level high energy laser system which is capable to deliver multiple wavelengths covering from visible to near infrared wavelength with tunable pulse duration from a few hundred microseconds up to a few hundred milliseconds. Some medical device companies make lasers to deliver parts of these requirements. In some devices, the user can switch handpieces connected to a console in order to produce two different laser wavelengths.

In terms of wavelength generation, some of the near infrared wavelengths, such as 755 nm, 1064 nm, 1320 nm, 1440 nm, or 1550 nm can be produced by direct laser emission from some well-known laser crystals including Alexandrite and rare earth ion doped crystals (i.e., $Nd^{3+}$, $Yb^{3+}$, or $Er^{3+}$). To obtain green laser (i.e., 532 nm or 524 nm), a two-step process is typically involved with the first step to generate 1064 nm or 1047 nm with Nd:YAG or Nd:YLF followed by the second harmonic frequency conversion with a nonlinear crystal (e.g., KTP or LBO). It should be mentioned that the methods for generating all these wavelengths are solid state laser based. However, yellow or orange wavelength is commonly produced with dye lasers thanks to the wide wavelength tunability of a laser dye. Clinically dye lasers represent one of the most successful laser technologies in dermatological applications, mainly treating vascular lesions. In addition to delivering a clinically preferred wavelength of 595 nm, it can easily deliver pulse energies greater than 15 J in 1 ms pulses, which are not possible with today's solid state crystal lasers. That said, dye lasers suffer from the required handling, re-filing, and disposal of toxic liquid dye solutions, short and finite pulse counts, and less pulse-to-pulse consistency in performance. To overcome these issues, a solid-state laser approach combined with frequency conversion technique may offer an alternative to produce decent energy in short pulses at 595 nm.

Compared with dye lasers, solid-state lasers have the advantages of small size, high efficiency, more robustness, and none of the toxic dyes used. Up to now, different solid state laser approaches have been employed to produce laser wavelengths in the yellow orange range. The first approach is direct emission from lasing medium. One example is Praseodymium ($Pr^{3+}$) doped YLF pumped with blue diodes made possible by recent development of this crystal in recent years. Watt level of power at 607 nm has been demonstrated with a slope efficiency of ~49%. However, the further power scaling is limited by the availability of high-power blue diodes. As another category, Raman laser with Neodymium ($Nd^{3+}$) doped gain medium is intended to shift ~1 um laser emission from Nd doped crystal to yellow wavelength with some Raman medium. Close to 5 W @ 588 nm has been reported for Nd:YLF based Raman laser. However, the relative low efficiency is becoming a technical challenge to further increase the power. And none come close to the required 12 kW.

Lasers with sum-frequency generation (SFG) represent the most studied approach for generating yellow and orange wavelengths. This approach involves generation of two wavelengths with at least one laser based on rare earth ion doped laser materials (i.e., ~1 um and 1.3 um). The lasers of these two wavelengths are then converted into yellow-orange wavelength via SFG with a nonlinear crystal, such as KTP, LBO, BIBO etc. When the laser is operated at quasi-CW or CW mode, intracavity SFG is typically employed to increase SFG efficiency with the cost of complex cavity arrangements and sensitive alignment since the fundamental lasers are coupled with the SFG. In another configuration, the fundamental lasers are Q-switched lasers with electro-optic (EO) or acousto-optic (AO) modulator(s) intending to increase the peak power to achieve better SFG efficiency. However, use of active Q-switch (EO or AO) leads to increased cost and alignment complexity. As another drawback of this configuration, temporal overlap of two Q-switched laser pulses needs high precision temporal synchronization mechanism with an accuracy of nanosecond. The electronic jittering or environment fluctuation may cause variations in temporal overlap of two fundamental laser pulses leading to lower frequency conversion efficiency and pulse-to-pulse instability.

Furthermore, the overall optical to optical efficiency may be lowered due to the Q-switching process. Worthy of special noting is that in either of the configurations (i.e., CW or Q-switching), two separate pumping sources (i.e., flash-lamps or diode lasers) were more commonly used to pump two laser cavities to generate fundamental wavelengths. The generation of maximized frequency conversion requires the temporal overlap between two laser pulses of two fundamental lasers, which is typically implemented by proper synchronization between the pump sources for each laser cavity as well. Such synchronization of two pump lasers typically results in complex electronic timing control and potentially instability of output energy due to the fluctuation of circuit jittering. For the configuration with Q-switching mechanism, the synchronization becomes even more complicated thanks to the addition of synchronization of Q-switching with two pump sources and nanosecond precision. Regarding the output power of yellow/orang laser, it is at least two orders of magnitude lower than that of a flashlamp pumped dye laser (i.e., >10 KW) although the record of ~90 W at 589 nm was reported with SFG of two fundamental lasers (i.e., 1064 nm and 1319 nm).

Therefore, high power (>kW)/high energy (Joule level) yellow-orange solid state laser with simple and stable configuration (without complex synchronization) is preferable over liquid dye lasers in order to suit the clinical need for treating larger and deeper vascular lesions. Similarly, the treatment of unwanted hair, pigmentation, as well as skin rejuvenation will be also benefitted with high energy at near infrared wavelength for effective and fast treatment.

BRIEF SUMMARY OF THE INVENTION

Disclosed, in one embodiment, is a high energy (Joule level)/high power (kW) and long pulsed solid state laser system which can deliver selectable multiple wavelengths ranging from visible to near infrared wavelengths through direct emission or nonlinear frequency conversion (i.e., second harmonic generation (SHG) and sum frequency generation (SFG)). A single long pulsed high energy (up to 60 J) and high-power laser (≥20 kW) is used to pump two solid state lasers to implement optical synchronization without introducing any control circuit. An unstable resonator design with a suitable optical arrangement for each laser cavity allows for achieving good beam quality (M2≤5) to ensure good focusability leading to high efficiency of nonlinear frequency conversion at high output energy. The output of high energy laser with switchable multiple wavelengths offers customized treatments for a wide range of skin conditions including vascular lesions, unwanted hair, pigmented lesions, and skin rejuvenation.

Disclosed is a novel apparatus to deliver high energy long pulsed laser energy with multiple user-switchable wavelengths ranging from visible to near infrared wavelength for customized treatment of various skin problems including vascular lesions, unwanted hair, pigmented lesions, and skin rejuvenation. The disclosed laser device is pumped with a single long pulsed (μs to ms) high energy (up to 60 J) laser with a power of >20 kW to implement optical synchronization of two rare earth ion doped laser medium to generate two near-infrared laser wavelengths at ~1 μm (i.e., 1.03-1.08 μm) and ~1.3 μm (i.e., 1.3-1.35 μm). The unstable cavity design is introduced to achieve both high energy and good beam quality (M2≤5) without using any mode selecting elements. The high energy and good beam quality makes it possible to achieve sufficient power intensity (>10 $MW/cm^2$) with good beam focusability for efficient SHG or SFG. The green (i.e., 515-540 nm) wavelength and red wavelength (e.g., 650-675 nm) can be obtained with SHG of fundamental laser at ~1 μm or ~1.3 μm, respectively. The generation of yellow or orange laser (i.e., 580-600 nm) can be implemented with SFG of two fundamental wavelengths (i.e., ~1 μm and ~1.3 μm). Altogether, this disclosed device can deliver six individual wavelengths (i.e., 700-980 nm, 1.03-1.08 μm, 1.3-1.35 μm, 515-540 nm, 650-670 nm, and 580-600 nm). It can also be configured to deliver a laser beam with blended wavelengths of two infrared lasers (i.e., ~1 μm and ~1.3 μm). The beam characteristics that can be delivered to the skin include single beam with adjustable spot sizes, microbeam array or blended beam profiles of two for different treatment needs. All the lasers of different wavelengths can produce the laser pulse variable from a few hundred us to a few hundred milliseconds determined by the pulse duration setting of pump laser.

Featured is an all solid-state laser system which combines direct laser emissions from two laser cavities followed by nonlinear frequency conversion and beam delivery assembly. The system is capable of delivering laser beams with switchable multi-wavelength and variable pulse duration empowered by optical synchronization. There are several unique capabilities including a version where a single high energy/high power pump laser is preferably used to pump two laser resonators to implement optical synchronization without a need to introduce a control circuit. Two laser resonators are preferably configured as unstable cavity arrangement to achieve high energy output with a good beam quality (M2≤5), which ensures the efficient nonlinear frequency generation (i.e., SHG or SFG) with adequate focusability. The free-running operation of two laser resonators without Q-switching offers compact and cost-effective design as well as the possibility to implement temporal synchronization optically without introducing expensive and complex control circuits. The free-running operation of two laser resonators also makes it possible to generate truly long pulsed output. The pulse duration can be easily tunable by adjusting the pulse duration of the pump laser.

The configuration of extracavity nonlinear frequency conversion (i.e., SHG or SFG) allows for simpler arrangement and easy alignment. The two near infrared wavelengths (i.e., ~1 μm and ~1.3 μm) can be generated from two laser resonators based on rare earth ion doped laser medium via direct emission, while the other three visible wavelengths are produced through SHG and SFG of two fundamental near infrared wavelengths. The laser medium of two laser resonators can be rare earth ion (i.e., $Nd^{3+}$ or $Yb^{3+}$) doped crystals or ceramic. The laser medium for two cavities may be the same type or different kinds.

The device may deliver joule level energy or kW level peak power at all the laser wavelengths including green, yellow-orange, red and near infrared, allowing for effective treatment of a broad range of skin conditions from vascular lesions, pigmentation, hair, and skin rejuvenation. The capability of delivering selectable wavelength and variable pulse duration allows for customized treatment of various indications. The disclosed device can deliver two laser pulses of different wavelengths with a predetermined time delay or simultaneously. The disclosed device can deliver blended beam patterns for different wavelengths (e.g., a solid beam at one wavelength superimposed with a fractionated microbeam pattern at another wavelength).

Featured is a multiple frequency laser system for treating skin conditions comprising a handpiece for treating skin conditions and a pump laser module having a single laser beam at a first frequency. A dual laser module receives the laser beam at the first frequency and includes dual free running laser resonators to produce a laser beam at a second frequency and a laser beam at a third frequency. A frequency conversion module receives as inputs the laser beam at the second frequency and the laser beam at the third frequency and is configured to selectively provide laser beams to the handpiece including a second harmonic generation of the second frequency, a second harmonic generation of the third frequency, a summed frequency generation of the second frequency and the third frequency, the laser beam at the first frequency, the laser beam at the second frequency, and/or the laser beam at the first frequency combined with the laser beam at the second frequency. The handpiece receives the laser beams from the frequency module and delivers them to skin for treatment with solid beam of variable size, a fractional microbeam pattern, or a hybrid beam pattern of a solid beam and fractional microbeams.

The system may further include a first optical subsystem for directly providing the laser output at the first frequency output by the pump laser to the handpiece for delivery to a patient's skin. The system may further include a second optical subsystem for directly providing the laser output at the second frequency, the laser output at the third frequency, and the laser output at the mixed second and third frequencies from the dual laser module to the handpiece for delivery to a patient's skin.

The pump laser is preferably a free running long pulsed high energy laser. The dual laser resonators may include laser mediums of different kinds or same types. The laser resonators may be free running lasers pumped simultaneously by the pump laser. The dual laser resonators can be configured as unstable cavities to achieve both high energy and good beam quality for efficient nonlinear frequency conversion. The dual laser resonators may contain rare earth ions doped crystals or ceramics as laser gain medium.

Frequency conversion can be implemented in an extracavity configuration. The frequency conversion module may include at least one non-linear optical crystal.

In one example, the first frequency is approximately 700-980 nm, the second frequency is approximately 1.03-1.08 μm, and the third frequency is approximately 1.3-1.35 μm. The laser output at the second harmonic frequency of second frequency may be approximately 515-540 nm and the laser output at the second harmonic frequency of the third frequency may be approximately 650-675 nm. The sum frequency of the second frequency and the third frequency may produce a laser beam at a frequency of approximately 580-600 nm.

The laser beam of mixed second frequency and third frequency can be delivered to the skin with a pre-determined delay or simultaneously. The laser system may deliver blended beam patterns for the second frequency and the third frequency. The laser system may deliver variable pulse durations ranging from a few hundred microseconds to hundreds of milliseconds, which can be controlled by tuning the pulse duration of pump laser.

Also featured is a multiple frequency laser method for treating skin conditions comprising: providing a laser beam at a first frequency; using dual free running laser resonators to produce, from the laser beam at the first frequency, a laser beam at a second frequency and a laser beam at a third frequency; and receiving the laser beam at the second frequency and the laser beam at the third frequency at a frequency conversion module and selectively providing laser beams to a handpiece including a second harmonic generation of the second frequency, a second harmonic generation of the third frequency, sum frequency generation of the second frequency and the third frequency, the laser beam at the first frequency, the laser beam at the second frequency, and/or the laser beam at the first frequency combined with the laser beam at the second frequency.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

Figures 4A, 4B:
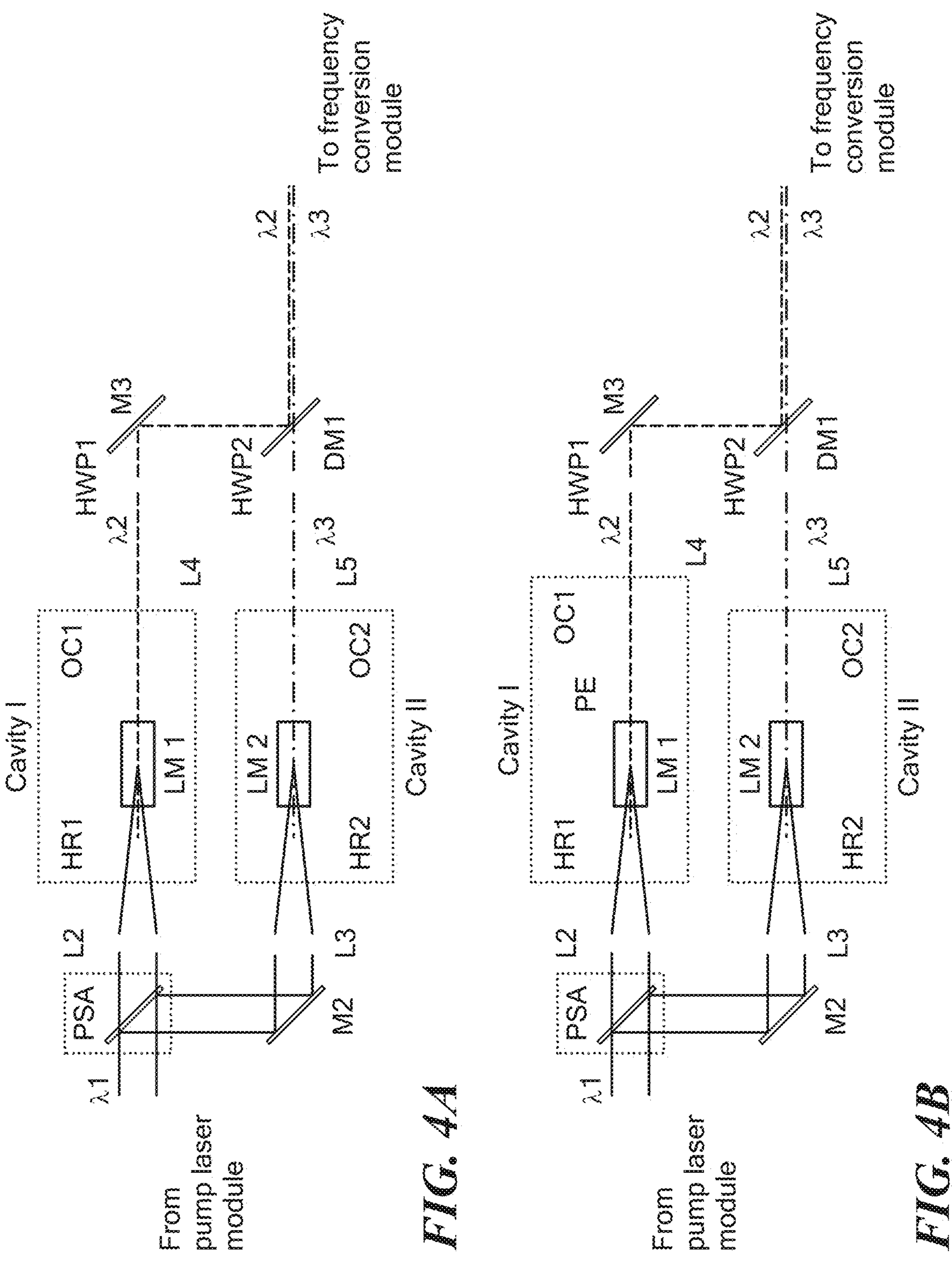
FIGS. 4A-B are schematic views of the dual laser module including two cavities with separate cavity mirrors (In FIG.
Figure 5A:
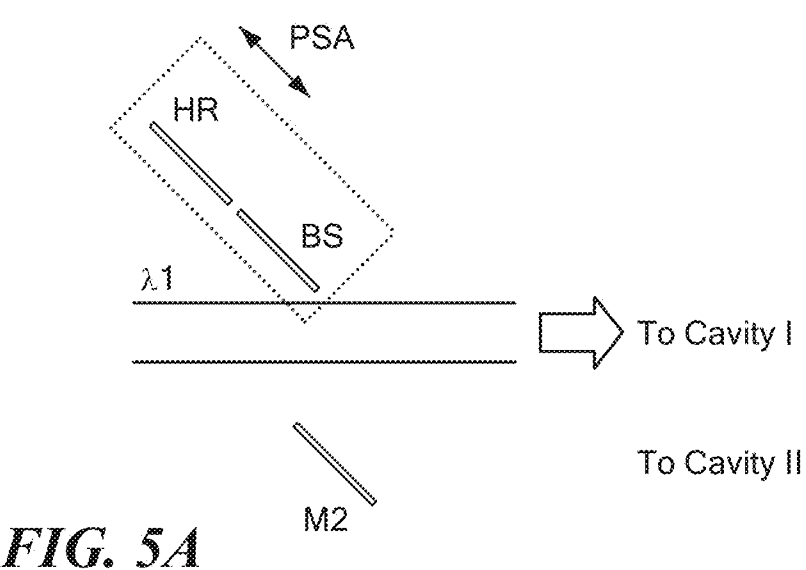
Figure 5B:
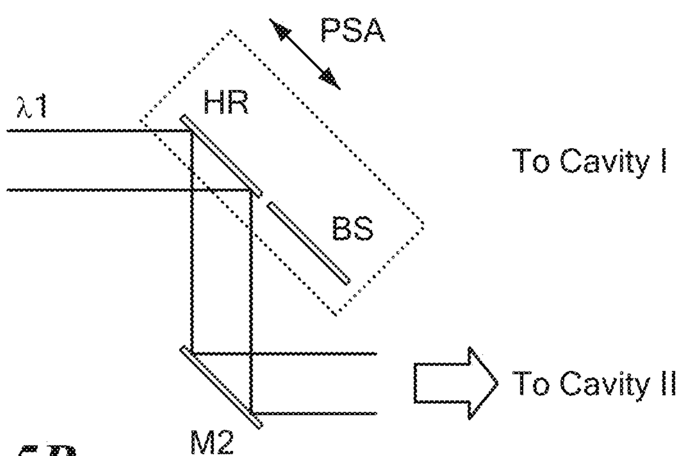
Figure 5C:
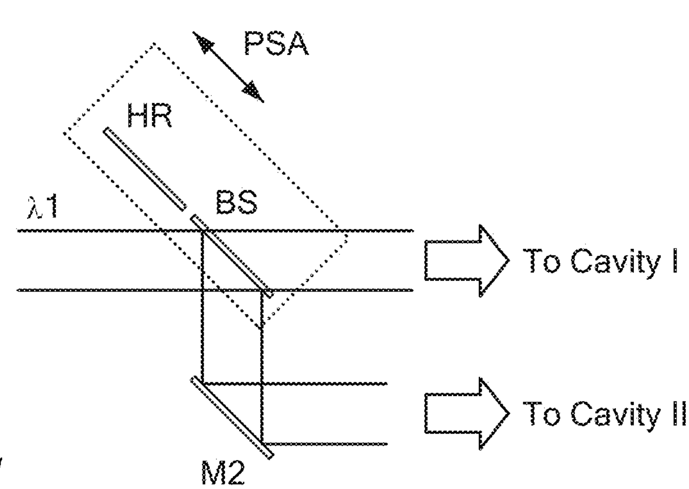
Figure 6:
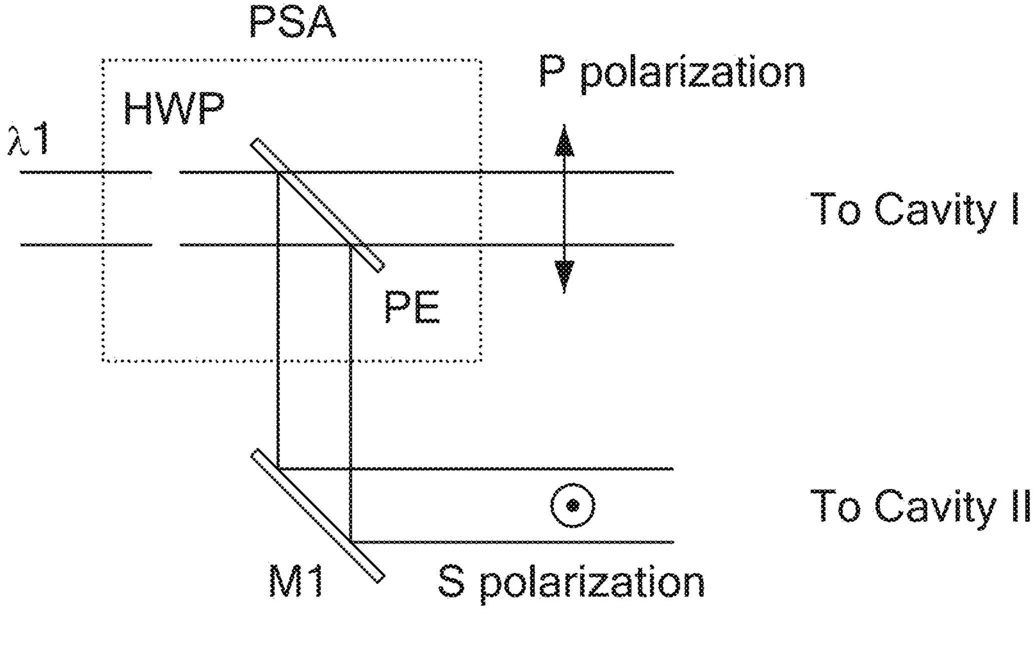
Figure 7:
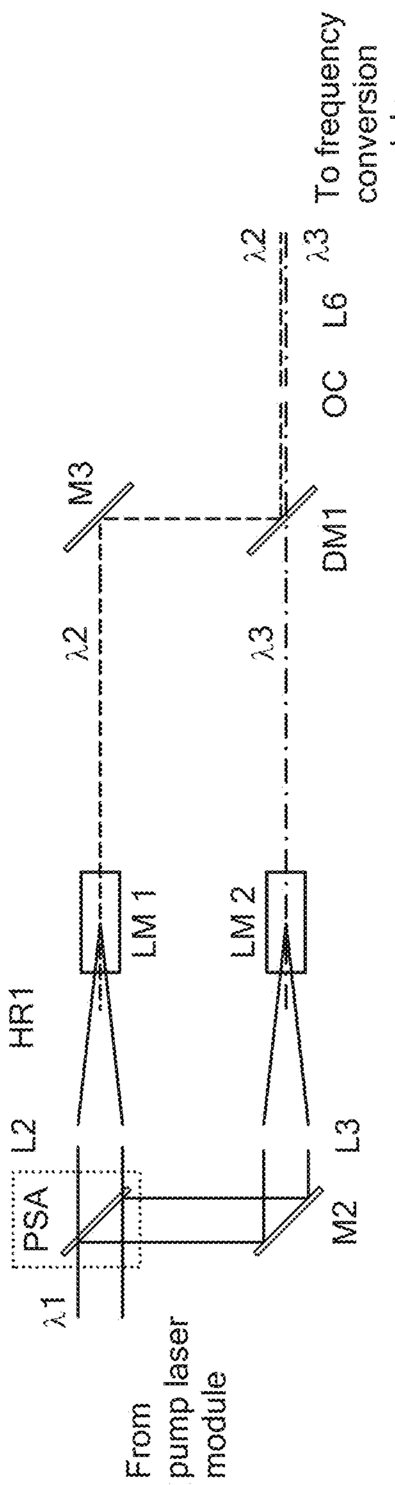
Figure 8:
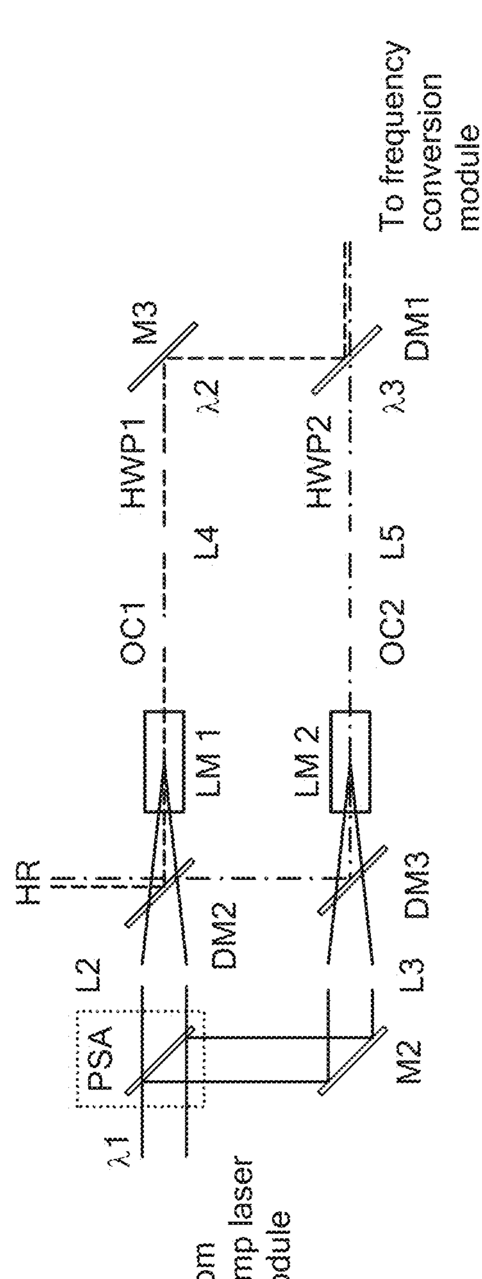
Figures 9, 10:
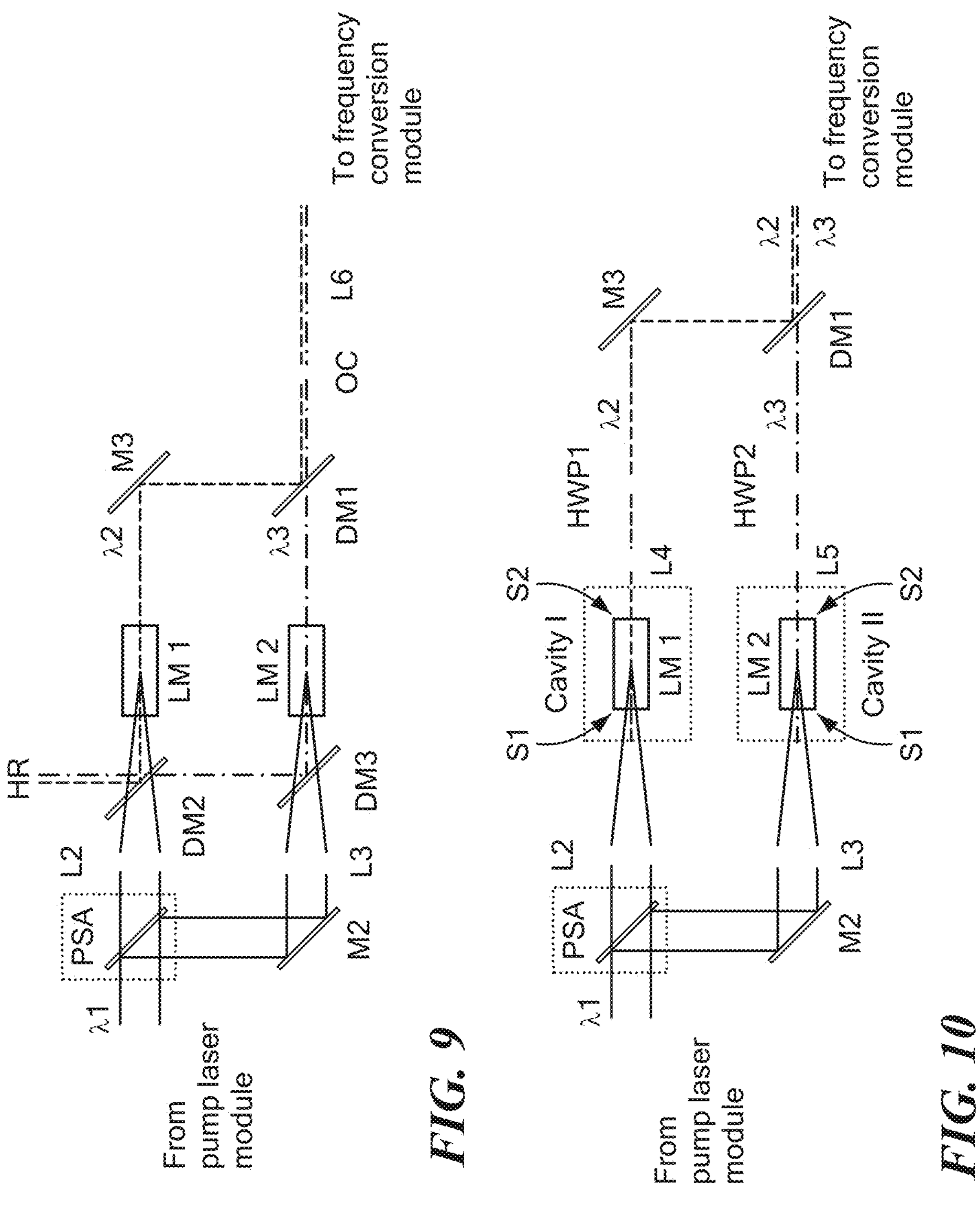
Figures 11, 12:
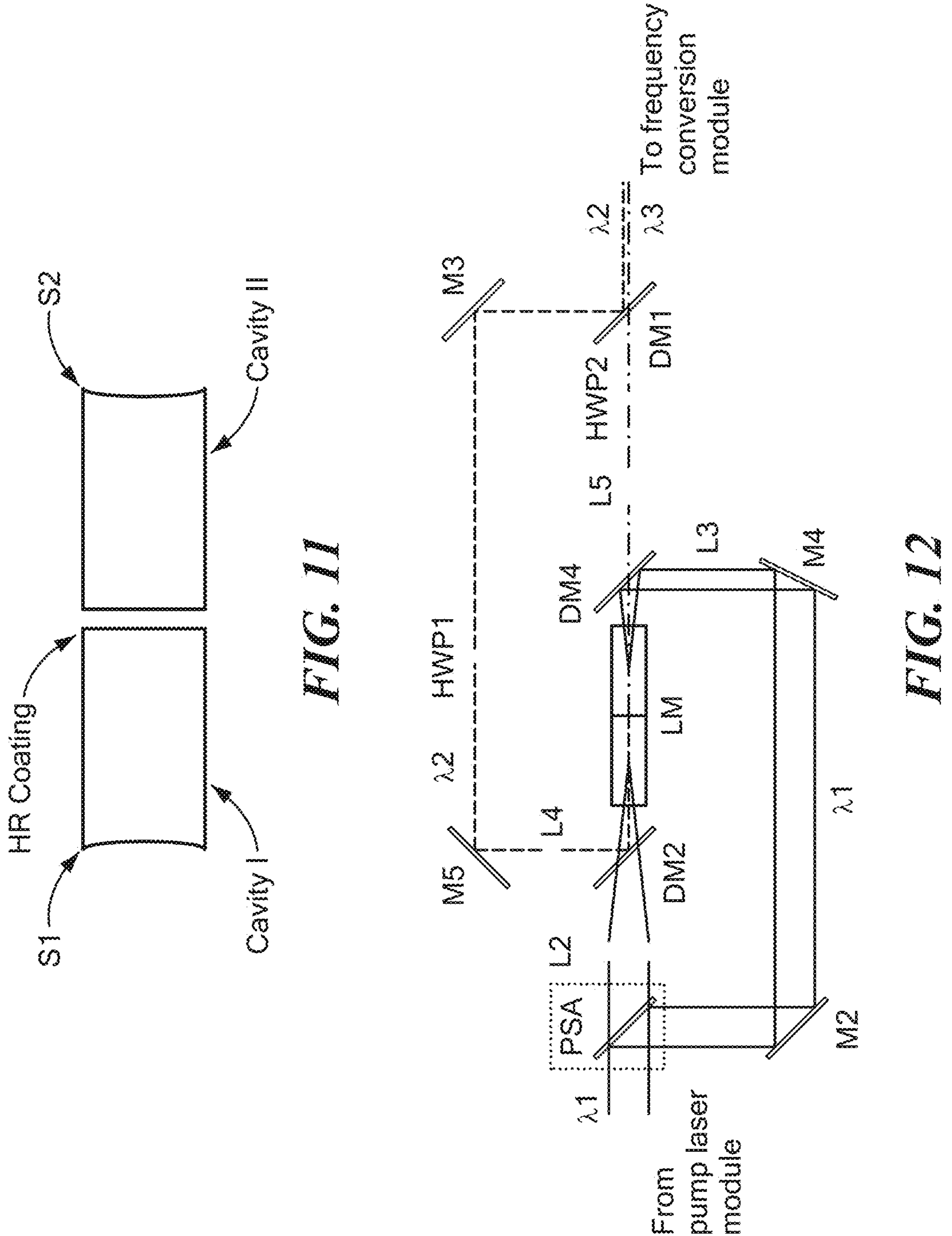
Figure 13:
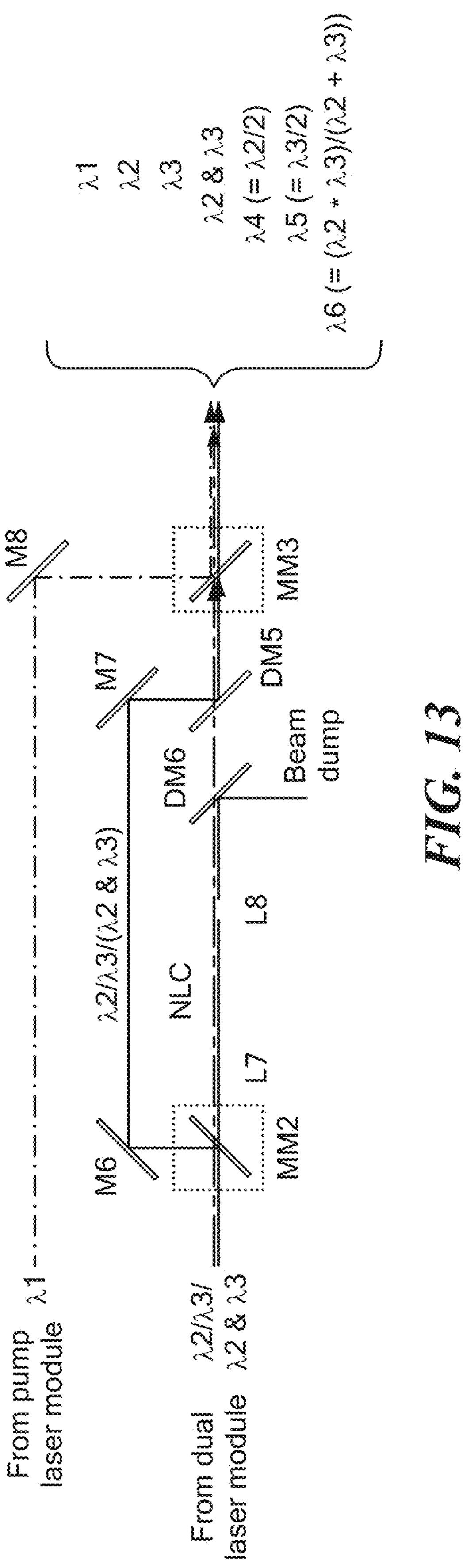
Figure 14A:
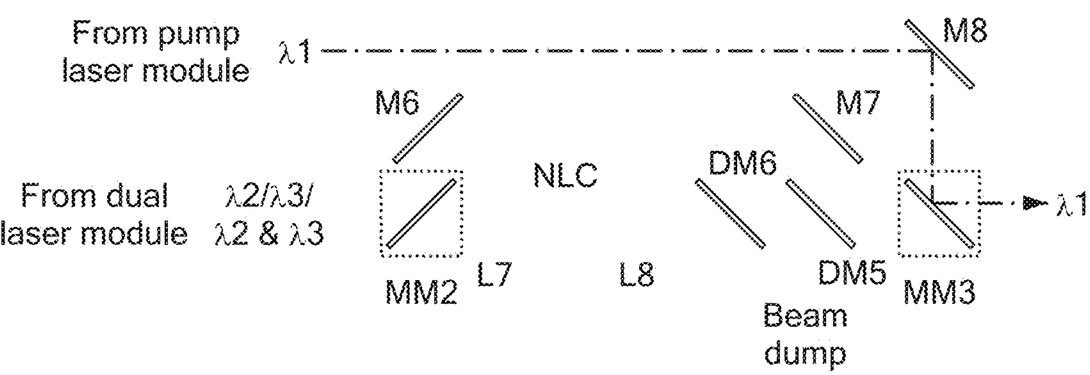
Figure 14B:
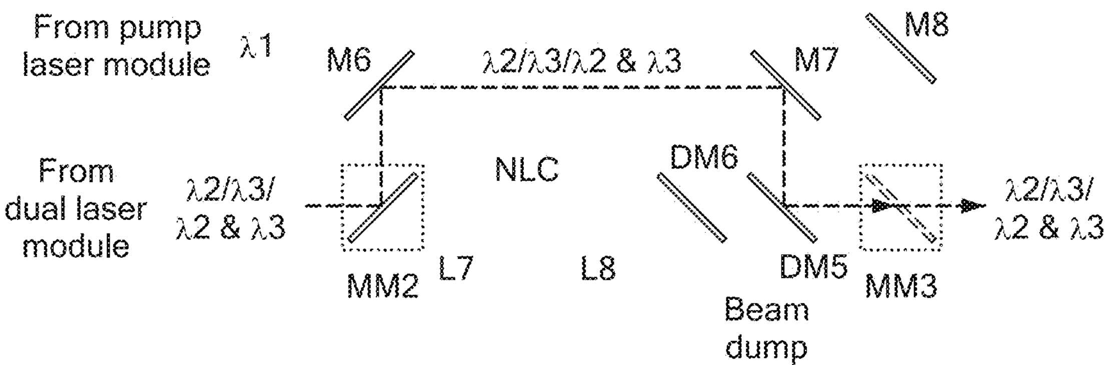
Figure 14C:
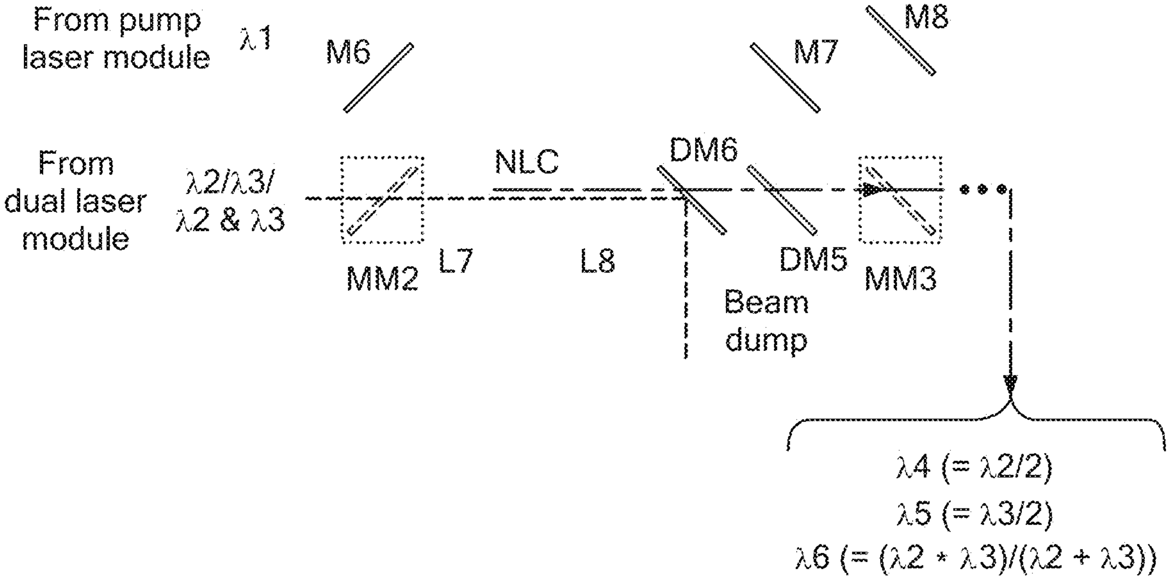
Figure 15:
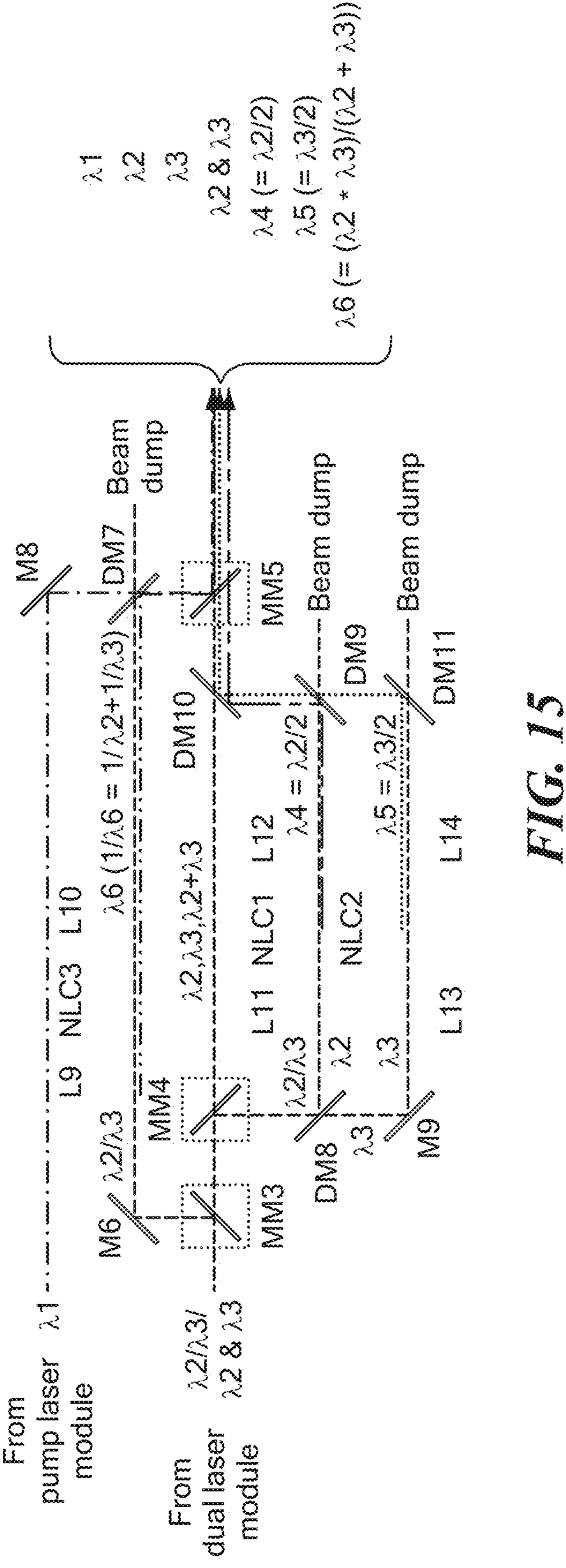
Figures 16A, 16B:
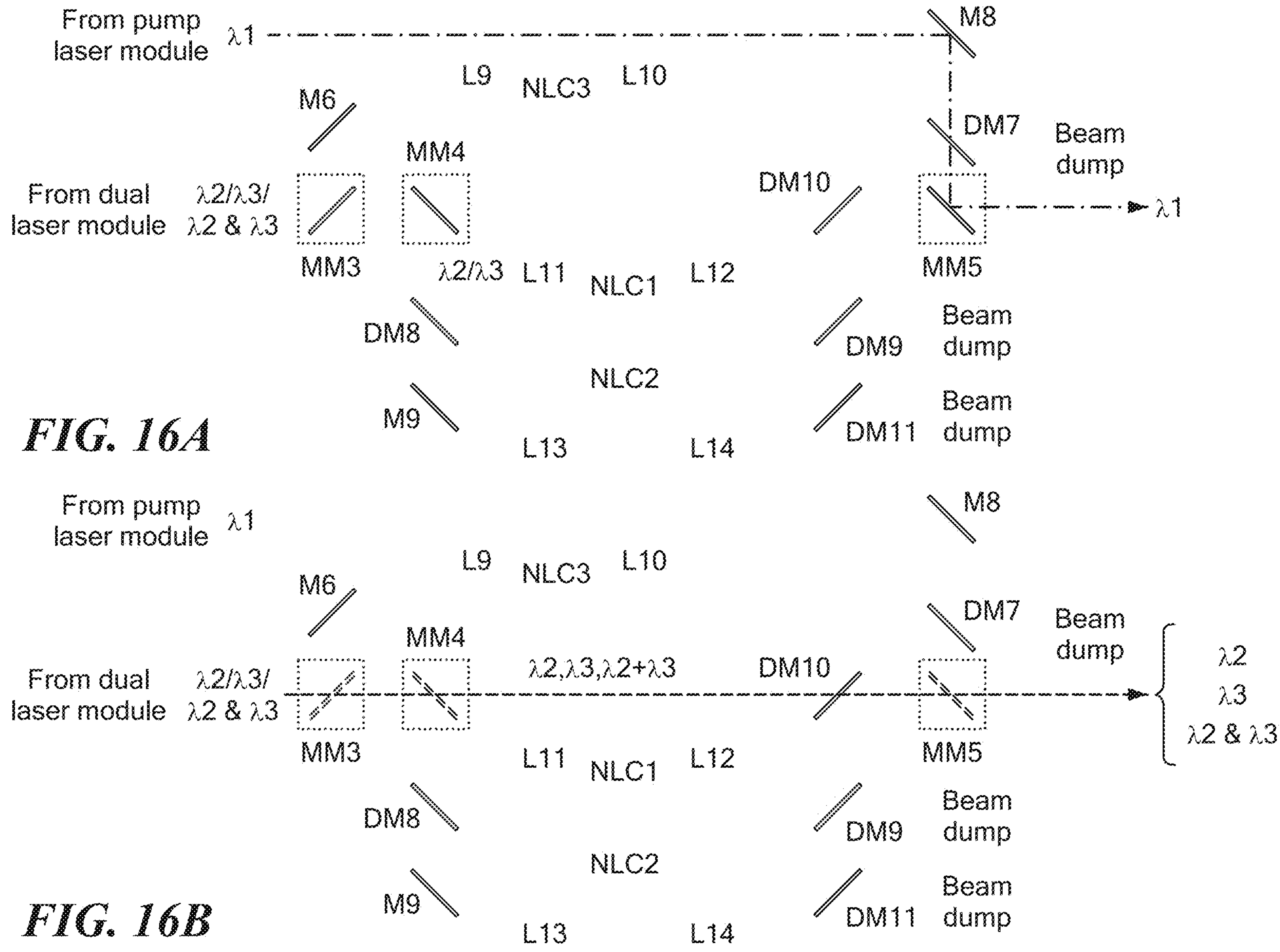
Figures 16C, 16D:
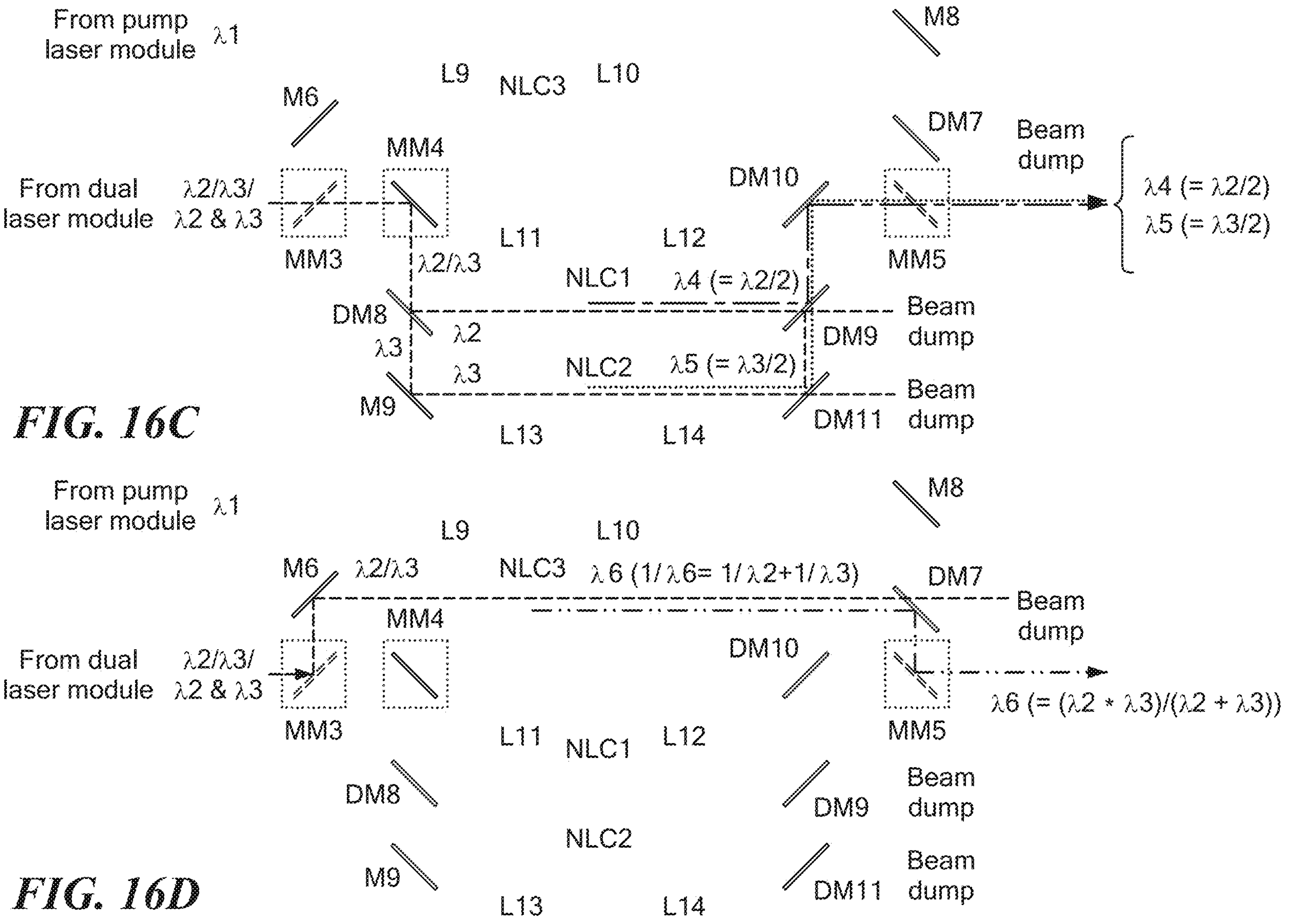
Figure 17A:
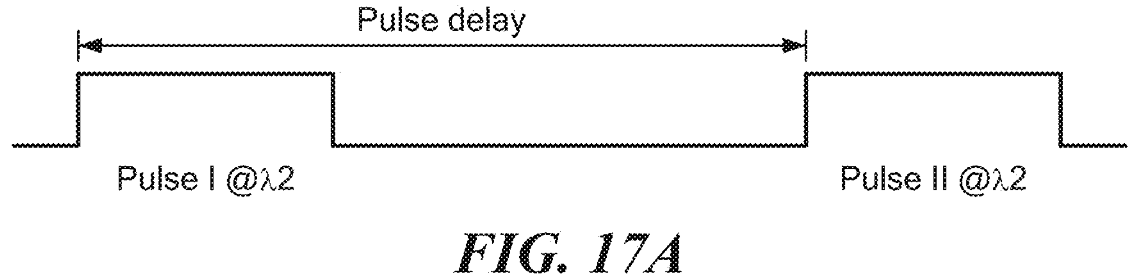
Figure 17B:
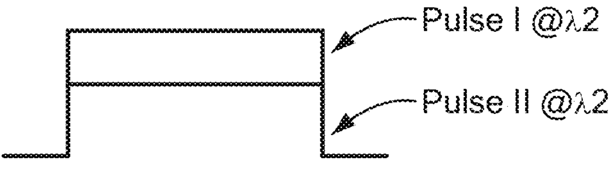
Figure 18:
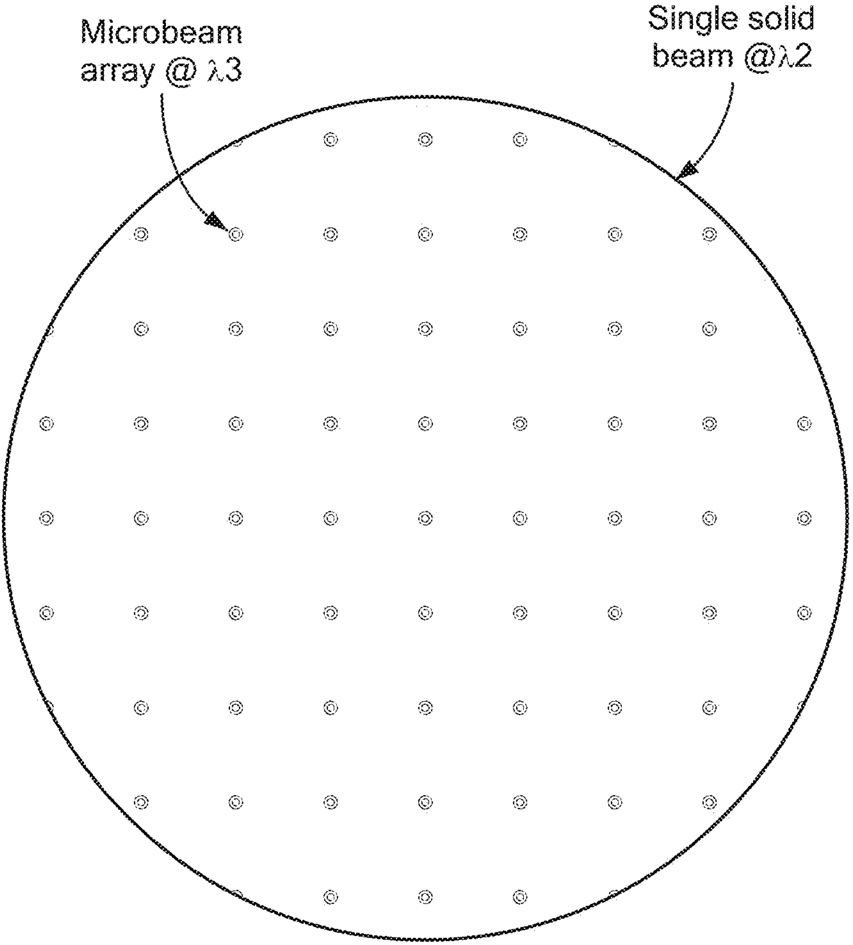
Figure 19A:
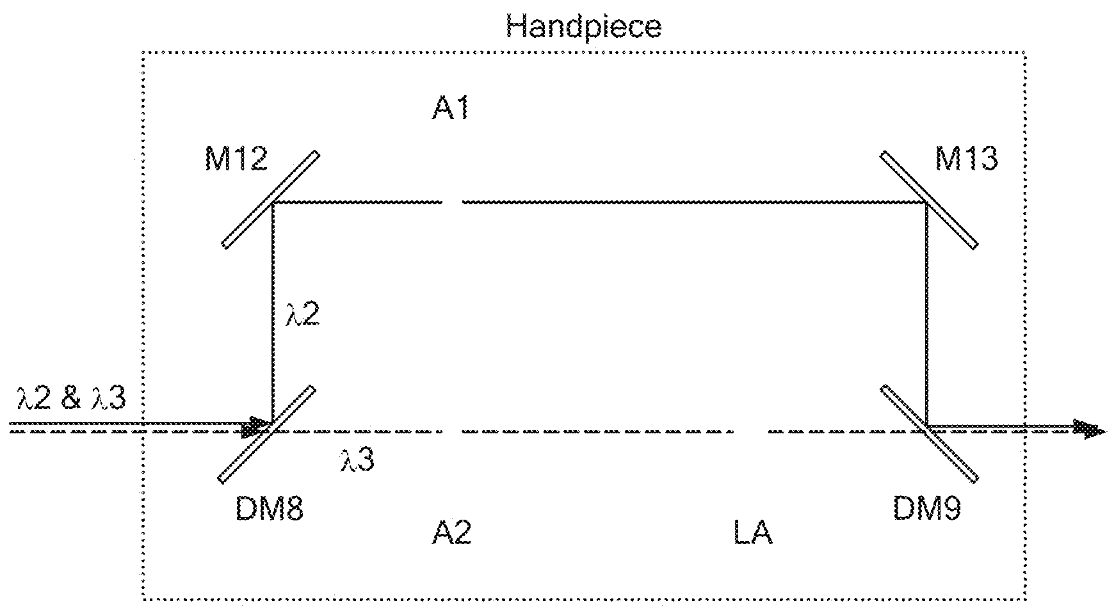
Figure 19B:
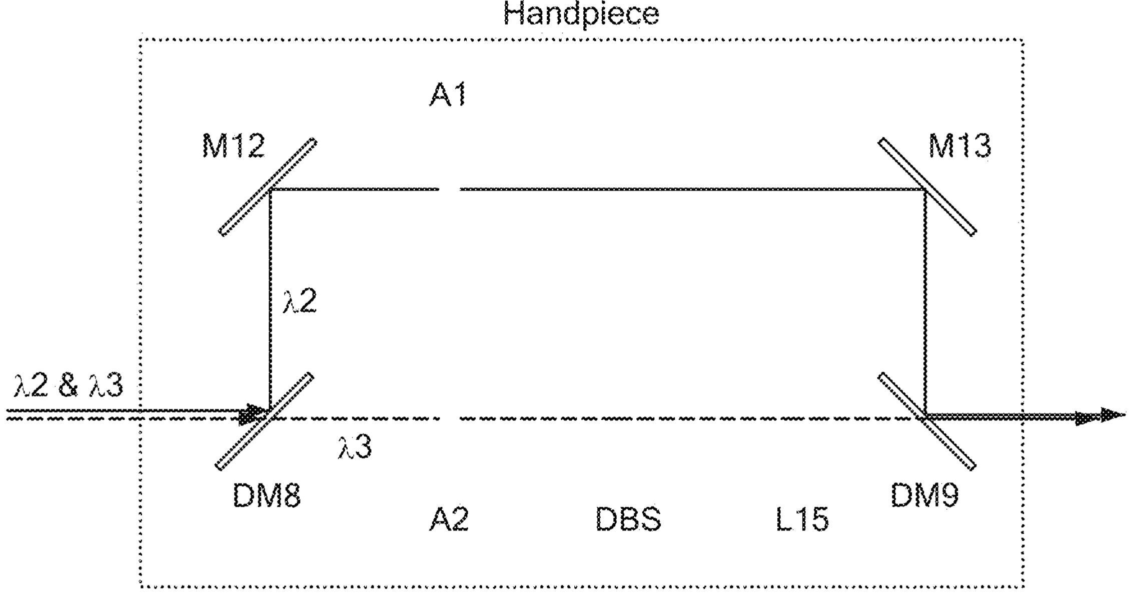

4A, the two laser mediums are an anisotropic material and in FIG. 4B, one of the laser mediums (i.e., LM1) is an isotropic material);

FIGS. 5A-C show examples of a pump beam steering assembly (PSA) for both non-polarized and polarized pump lasers;

FIG. 6 shows an example of pump beam steering assembly (PSA) for a linearly polarized pump laser;

FIG. 7 is a schematic view of a dual laser module including two cavities with a common output coupler;

FIG. 8 is a schematic view of a dual laser module including two cavities with a common HR mirror;

FIG. 9 is a schematic view of a dual laser module including two cavities with the same HR mirror and output coupler;

FIG. 10 is a schematic view of a dual laser module including two monolithic cavities;

FIG. 11 is a representation of a composite monolithic laser rod;

FIG. 12 is a schematic view of a dual laser module including a composite monolithic laser rod;

FIG. 13 shows a frequency conversion module with a single crystal for nonlinear frequency generation;

FIGS. 14A-C show frequency conversion modules with different wavelength selection modes for the output, a single wavelength λ1 (FIG. 14A); single wavelength λ2, λ3 or blended wavelengths of λ2 and λ3 (FIG. 14B); and three visible wavelengths (i.e., λ4, λ5, and λ6) generated from nonlinear frequency conversion (FIG. 14C);

FIG. 15 shows a frequency conversion module with three crystals for nonlinear frequency generation;

FIGS. 16A-D are schematic views of a frequency conversion module with different delivered wavelength modes: a single wavelength λ1 (FIG. 16A); single wavelength λ2, 13; or mixed wavelengths of λ2 and λ3 (FIG. 16B); λ4 or λ5 generated by second harmonic frequency conversion of λ2 or λ3, respectively (FIG. 16C); and λ6 generated from sum frequency conversion of λ2 and λ3 (FIG. 16D);

FIGS. 17A-B show delivery of dual pulsed lasers in sequence with a certain time delay (FIG. 17A) or simultaneously (FIG. 17B);

FIG. 18 shows delivery of blended beam profiles for the lasers with mixed wavelengths; and FIGS. 19A-B show representations of handpieces used to deliver blended beam profiles to skin (In FIG. 19A, a lens array is used and in FIG. 19B, a diffractive beam splitter is used).

DETAILED DESCRIPTION OF THE INVENTION

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

Figure 1:
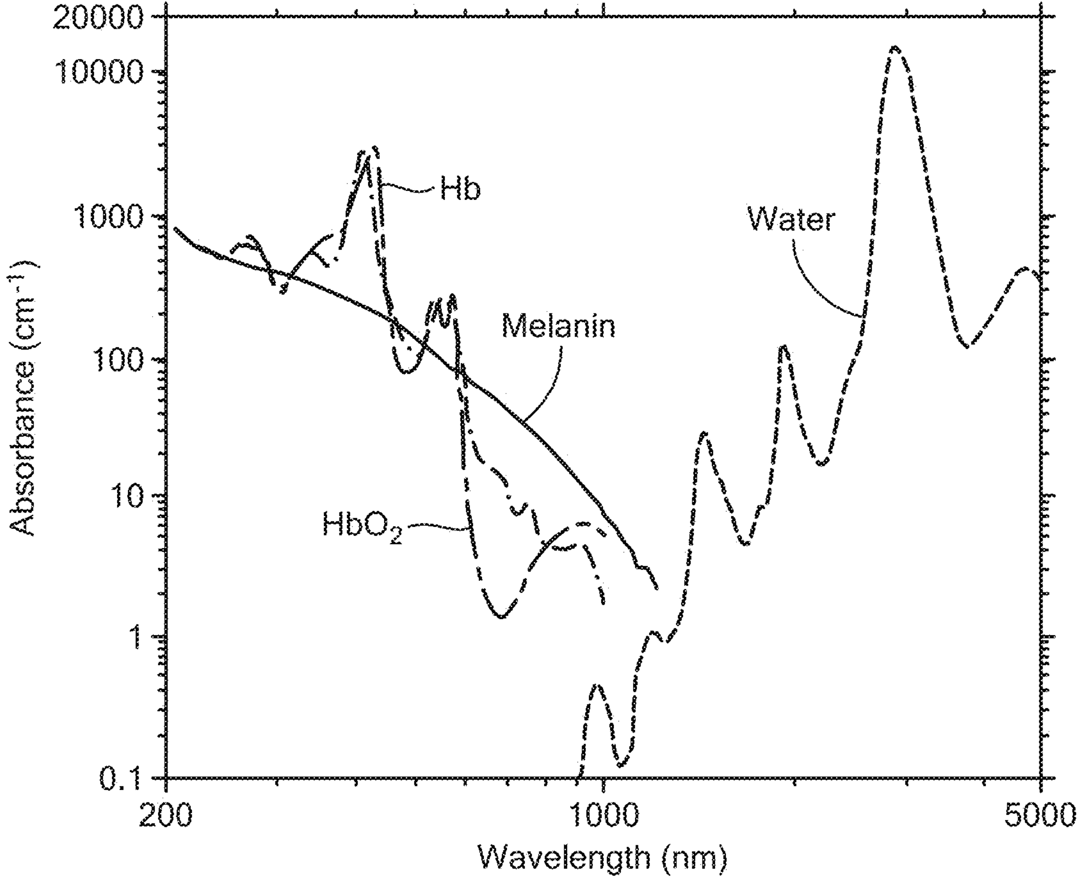
FIG. 1 is a graph of the absorption spectra of several major chromophores present in skin.
Figure 2A:
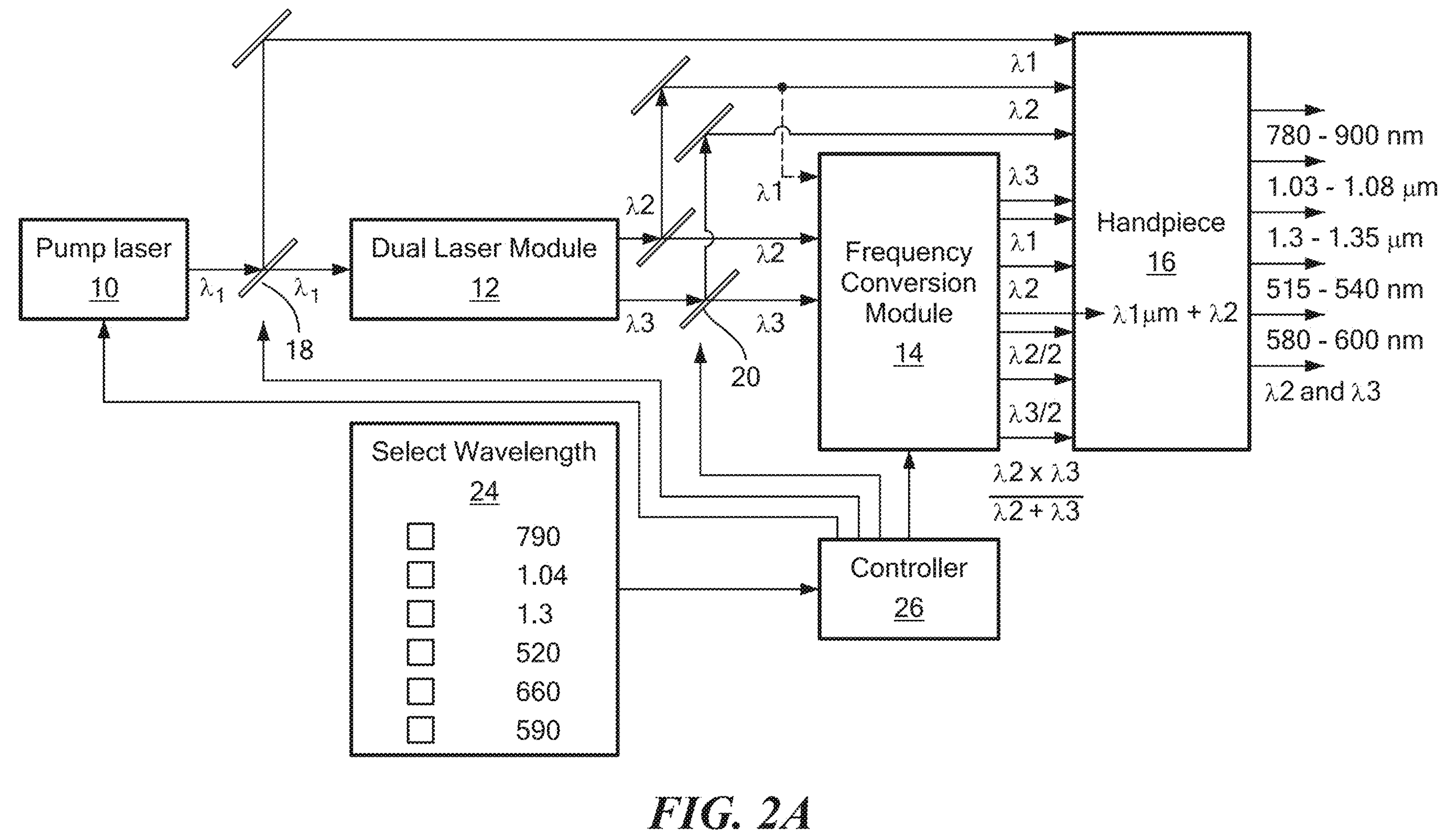
FIGS. 2A-2B are schematic block diagrams of the system architecture of one preferred solid-state laser system.

In one example shown in FIG. 2A, a single pump laser 10 has a laser output at a first frequency directed to dual laser module 12 which produces a laser output at a second frequency and another laser output at a third frequency. Frequency conversion module 14 receives, as inputs, the laser output at the second frequency and the laser output at the third frequency from dual laser module 12 and is configured to selectively provide laser outputs to handpiece 16 which are second harmonic generation (SHG) of the laser output at the second frequency, a SHG of the laser output at the third frequency, the laser output at sum frequency generation wavelength of the second frequency and the third frequency, the laser output at the first frequency, the laser output at the second frequency, and/or the laser output at the first frequency combined with the laser output at the second frequency.

In one example, a first optical subsystem 18 is configured for providing the laser output at the first frequency directly to handpiece 16 and a second optical subsystem 20 can be configured for providing the laser output at the second frequency and the laser output at the third frequency from the dual laser module 12 directly to the handpiece 16 for delivery to a patient's skin. In other embodiments, the laser output from the pump laser 10 and the laser outputs from dual laser module 12 are provided to frequency conversion module 14 but no conversions are made and thus the laser output of the first, second, and third frequencies are directed to handpiece 16 without frequency conversion.

The pump laser 10 is preferably a long pulse high energy laser. The dual laser module 12 may include two laser resonators each configured as a laser medium. The frequency conversion module may include at least one nonlinear optical crystal. In one example, the first frequency is 700-980 nm, the second frequency is 1.03-1.08 μm, and the third frequency is 1.3-1.35 μm. In one example, the SHG of the laser output of the second frequency is 515-540 nm and the SHG of the laser output of the third frequency is 650-675 nm. The SFG of the laser output at the second frequency and the laser output at the third frequency. The SFG may produce a laser beam at a frequency of 580-600 nm. In some examples, wavelength outputs by the handpiece may be 593 nm, 755 nm, 1064 nm, and 1342 nm.

FIG. 2A also shows input/output section 24 (including, for example, a touch screen) allowing the user to select one or more specific wavelengths and, in response, controller 26 controls frequency conversion module 14 and also optical subsystems 18 and 20 in order for the handpiece to receive the chosen wavelength(s) to be delivered to the patient's skin. Controller 26 may be a processor, microcontroller, computer, or the like programmed with software instructions stored in memory.

Figure 2B:
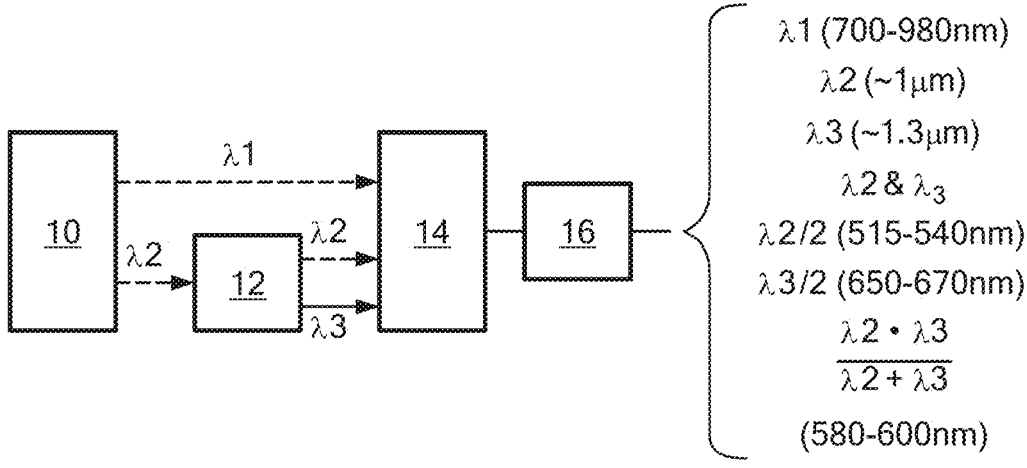

One exemplary apparatus comprises four main modules including a pump laser module, a dual laser module, a frequency conversion module, and a treatment handpiece. FIG. 2B is a block diagram of an exemplary system architecture. Briefly, pump laser 10 is a single laser source which can deliver more than 60 J and 20 kW peak power at long pulsed mode (i.e., a few hundred microseconds to a few hundred milliseconds) at a wavelength of λ1. The dual laser module 12 receives the pump laser and produces two near infrared wavelengths, λ2 and λ3 (i.e., ~1 μm and ~1.3 μm) via direct lasing emission from two laser resonators. Frequency conversion module 14 takes the lasers of two wavelengths generated from the previous module as well as pump laser as two inputs, and selectively direct seven laser outputs of different wavelengths. i.e., λ1, λ2, λ3, mixed λ2 and λ3, λ2/2, λ3/2, and (λ2*λ3)/(λ2+λ3) as outputs. The first four outputs are implemented with proper beam steering optics while the rest are generated through nonlinear frequency conversion (i.e., SHG or SFG) with at least one nonlinear crystal. As the last function group, a handheld module (i.e., treatment handpiece 16) will deliver the seven laser beams with different beam characteristics (i.e., single beam with adjustable spot sizes or microbeam array) for different treatments.

The Pump Laser Module

Figure 3A:
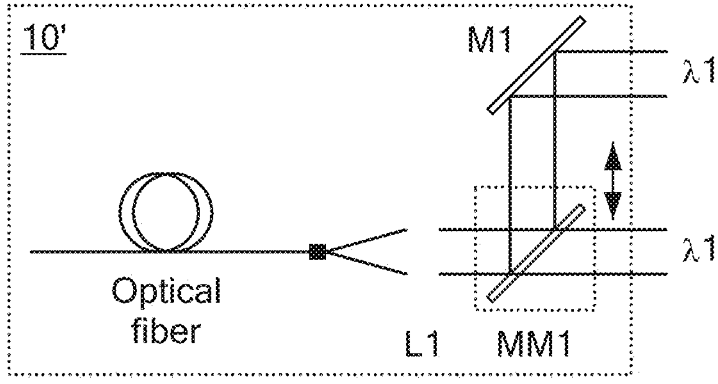
FIGS. 3A-C are schematic views of a pump laser module.
Figure 3B:
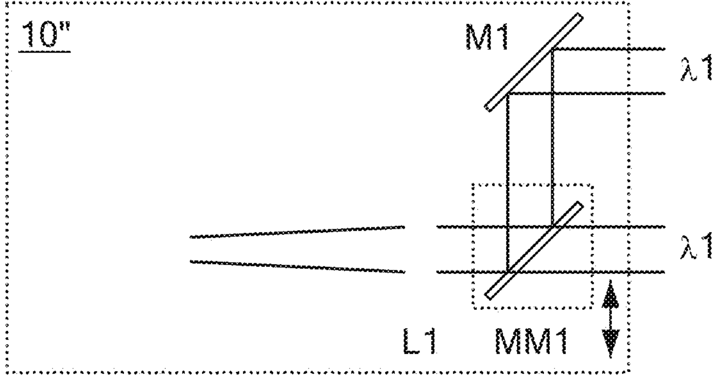
Figure 3C:
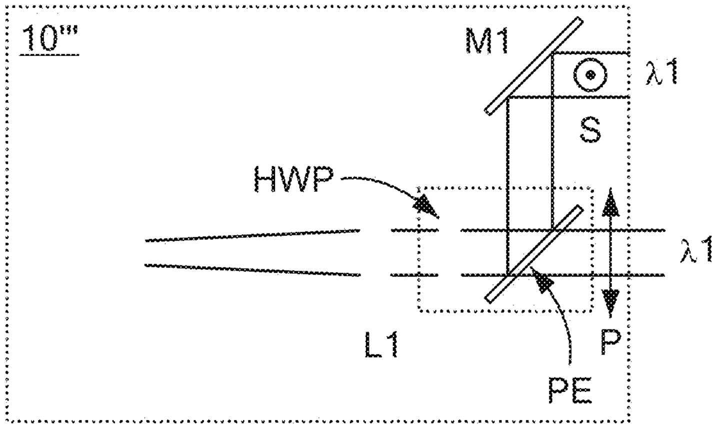

The pump laser module preferably hosts a long pulsed high energy (≥60 J) laser, which can deliver more than 20 kW peak power at a pulse duration variable from a few hundred microsecond to a couple of hundred milliseconds (see FIG. 3). In one example, the energy level is between 200 mJ and 20 J and the pulse duration is 0.5 ms to 100 ms. Its wavelength, λ1 typically matches the absorption of the rare earth ion doped laser medium in the two laser resonators in the next module. For example, this laser may be a flashlamp pumped Alexandrite laser emitting 60 J (or ≥20 kW) laser at around 753 nm±3 nm. In an alternative example, the pump laser may be a high-power diode laser, which emits laser in the range of 800-980 nm. The choice of the exact pump wavelength is determined by the match of the absorption of a specific laser medium. The pump laser generates pump laser pulses at λ1 that can be delivered with a multi-mode fiber (i.e., FIG. 3A) or in free space to a collimating lens L1 (i.e., FIG. 3B). The collimated pump beam further propagates to a movable mirror MM1, whose position can be configured to be either in the beam path or out of the beam path. When MM1 is positioned to be in the pump beam path, it will redirect the beam directly to the frequency conversion module and become one of the final laser output wavelengths (i.e., λ1) in combination with a mirror (i.e., M1). In the case where the movable mirror is driven to be out of the beam path, the collimated pump laser will be delivered to the next module, dual laser module as a pump source. So, the pump laser module can be configured with two output ports with one for direct output at λ1 and the other for pumping the dual laser module. Worthy of special noting is that such a movable mirror can be a mirror on a rotary stage, or a translation stage. In the case of a polarized pump laser beam in free space (e.g., configuration B), MM1 can be a polarizing element(s) to selectively direct the pump beam to either port based on the polarization characteristic of incident beam. In one embodiment, this polarizing element can be a combination of a rotational half waveplate and a polarizer cube or thin film polarizer, shown in FIG. 3C. The half waveplate, HWP is mounted on a rotary stage and can rotate the linearly polarization orientation. When the pump laser is turned into P polarized, it will pass through the polarizing element to pump the dual laser module without any reflection loss. In case when S polarized pump beam is obtained with the half waveplate, all the pump energy will be reflected by the polarizing element and M1 as another output of this module.

The Dual Laser Module

The dual laser module is one functional module of the system. As shown in FIG. 2, It receives the collimated pump laser at λ1 to energize two laser resonators to generate two laser beams at wavelengths of λ2 and λ3. These two wavelengths are in near infrared range with one about 1 μm (i.e., 1.03-1.08 μm) and the other around 1.3 μm (i.e., 1.3-1.35 μm). The laser medium for the two laser resonators, i.e., LM1 and LM2 may be rare earth ion doped laser material. In some embodiments, the dopant can include neodymium ($Nd^{3+}$) or Ytterbium ($Yb^{3+}$). The host material can include Yttrium Aluminum Garnet (YAG), Yttrium Aluminum Perovskite (YAP), Yttrium Vanadate ($YVO_4$), Yttrium Lithium Fluoride (YLF), Yttrium Scandium Gallium Garnet (YSGG), Gadolinium Scandium Gallium Garnet (GSGG), or Gadolinium Vanadate ($GdVO_4$) in crystal-line form. In other examples, the host material can be amorphous structure, i.e., ceramic material. It should be mentioned that LM1 and LM2 can be two different laser materials or the same material. If the same laser material is used for two laser cavities, it is capable of selectively emitting dual wavelength lines (i.e., ~1 μm and ~1.3 μm). Table 1 lists some typical examples of the laser materials that can be used in the system. For example, the laser can include a Nd:YAG gain medium to generate 1.064 μm laser while a different laser crystal Nd:YAP or Nd:$YVO_4$ to generate 1.342 nm laser. As shown in Table 1, although multiple laser mediums can produce wavelengths in these two regions, the choice of laser medium depends on various factors including material properties (i.e., thermal conductivity, thermal expansion, birefringence, temperature dependence of refractive index, mechanical stress, etc.), available size, and cost.

TABLE 1 examples of commonly used laser materials for near infrared wavelength generation.

| Laser medium | | λ1, μm | λ2, μm |
|---|---|---|---|
| Nd:YAG | | 1.064 | 1.319 |
| Nd:YVO4 | | 1.064 | 1.342 |
| Nd:YLF | π | 1.047 | 1.321 |
| | σ | 1.053 | 1.313 |
| Nd:YAP | a-axis | 1.064 | 1.339 |
| | c-axis | 1.079 | 1.342 |
| Yb:YAG | | 1.030 | — |

The dual wavelength lasers can be configured in several different ways based on different optical arrangements of two laser resonators. Several examples of these configurations are described as follows.

Configuration A: Two Cavities With Separate Cavity Mirrors

In this configuration, the dual laser module hosts two laser resonators with each of them having separate high reflector and output coupler. As shown in FIG. 4A, the collimated pump laser at λ1 is selectively directed to either Resonator I or Resonator II or both. Different pumping modes will generate different wavelengths. More specifically, the pumping of Resonator I can produce a laser beam at a wavelength of λ2 while the pumping of Resonator II can generate another laser beam at a wavelength of λ3. The two wavelengths of λ2 and λ3 can also be generated simultaneously if both resonators are pumped by a split pump energy to each resonator.

The pump laser beam(s) is directed into one of the laser resonators or both through focusing lens, L2 or L3 to provide proper spot size to achieve optimized laser efficiency. Each cavity has its own cavity mirrors, i.e., high reflector, HR1/HR2 and output coupler, OC1/OC2. HR1 or HR2 have coatings to highly transmit pump laser into laser resonator and highly reflect new laser wavelength (i.e., λ2 or λ3) to facilitate laser oscillation, respectively. OC1 and OC2 are partial reflectors as output couplers for lasers at λ2 and λ3, respectively. LM1 and LM2 are the laser medium for Resonator I and Resonator II, respectively. If a laser medium is anisotropic in nature (e.g., rare earth ion doped YLF and $YVO_4$), the generated laser is linearly polarized. Therefore, there is no need to introduce any polarizing element in the cavity to select a preferrable polarization as an output. This case is shown in FIG. 4A, in which both laser mediums LM1 and LM2 are birefringent. However, if an isotropic laser medium (e.g., rare earth ion doped YAG) is used in a resonator, a polarizing element (i.e., PE) has to be added to favor only one preferred polarization to oscillate and become an output. FIG. 4B depicts this scenario. In order to achieve good beam quality at high output energy, unstable cavity design is applied to the arrangement of two resonators. In this application, we propose a simple scheme to implement unstable cavity operation. Specifically, the unstable cavity is formed by a plano HR mirror (i.e., HR1 or HR2) and a convex output coupler (i.e., OC1 or OC2). The use of convex output coupler is a simple way to improve beam quality (i.e., M2) of the generated laser beam by filtering out higher order modes without introducing additional mode selection element(s) to complicate the cavity alignment as well as to add more cost. Typically, the sharper curvature of OC mirror will lead to better beam quality with the penalty of output energy. An optimized cavity design is the one with a good balance of high energy with adequate beam quality (M2≤5). To optimize overall laser performance at two wavelengths aiming for best nonlinear frequency conversion (primarily SFG) in the next step, choice of several parameters should be considered.

These parameters include pump beam splitting ratio, focal lengths of L2 and L3, reflectivity and curvatures of output couplers, laser crystal specifications (i.e., doping concentrations, lengths, and locations). The output laser beams from two resonators are typically divergent. They will be collimated with a collimating lens, L4 or L5 for each resonator. Each collimated new laser beam passes through a half waveplate (i.e., HWP1 or HWP2) before combined with a dichroic mirror, DM1. The use of one half waveplate for each laser beam (λ2 or λ3) is intended to adjust the polarization of two beams to achieve phase matching for nonlinear frequency conversion. The two laser beams at λ2 and λ3 propagate collinearly after the beam combiner DM1 and are delivered to the frequency conversion module.

The selectivity of different pump modes can be implemented by a pump beam steering assembly, PSA. FIG. 5 shows an example of optical arrangement of PSA. It can include a translation stage with two mirrors mounted on it. One mirror, HR has a high reflecting coating at λ1 and the other optic, BS, is a beam splitter, which can split part of pump beam to be directed to Resonator I via transmission and the rest of pump energy to Resonator II via reflection. The splitting ratio of pump laser energy to Resonator I to that to Resonator II is determined by optimizing the output energies from two resonators for achieving the maximum frequency conversion, primarily sum frequency generation. The PSA assembly has three positioning stops. When the translation stage is positioned at a stop (FIG. 5A) where none of mirrors are in the pump beam path, all the pump laser energy is directed to Resonator I and only one wavelength λ2 is produced. When the HR mirror is placed in the pump beam path (FIG. 5B), the incoming pump beam will be completely reflected by HR and further directed by a mirror, M2 to pump Resonator II to generate laser at λ3. At the last stop (FIG. 5C), the beamsplitter BS is positioned in pump beam path allowing pumping two resonators simultaneously. In this case, two laser wavelengths will be generated. It should be mentioned that this pump beam steering configuration can be used for both the polarized and non-polarized incident pump laser.

In other words, it can work for both configurations of pump beam module (i.e., fiber coupled pump laser (FIG. 3A) and free space delivered pump laser (FIG. 3B). In another example, the pump beam steering can be implemented by the combination of a half waveplate, HWP, and a polarizing element in case the pump laser is linearly polarized (see FIG. 6). The half waveplate is mounted on a rotary stage and can rotate the linearly polarization orientation. When the pump laser is turned into P polarized, it will pass through polarizing element without any reflection loss. So only Cavity I is selectively pumped and only λ2 will be generated. In case when S polarized pump beam is obtained with the half waveplate, all the pump energy will be reflected by the polarizing element to pump Cavity II to produce λ3. If the polarization of pump laser is tuned to be somewhere in between P and S polarizations, the incoming pump beam will be split into P and S polarizations to pump both cavities. For the case where equal pump energy is needed to pump two cavities, the polarization of the pump beam should be rotated to be 45 degrees related to S or P polarization direction.

With the pump beam steering selector, PSA, this module is capable to deliver the near infrared lasers in three modes, single wavelength λ2, single wavelength λ2, and blended wavelengths of two. In some examples, a 60 J and 20 kW Alexandrite laser is employed as a single pump source. The module with Nd:YAG and Nd:YAP materials can deliver roughly 30 J output at 1.064 μm from Nd:YAG resonator, around 25 J output at 1.342 μm from Nd:YAP resonator or two wavelengths (i.e., ~15 J @1.064 μm and ~13.5 J@1.342 μm) simultaneously.

Configuration B: Two Laser Cavities Sharing One Common Output Coupler

This configuration is the variant of Configuration A. As shown in FIG. 7, two cavities share one common output coupler, OC but with separate high reflector, HR1 or HR2. The use of one convex output coupler OC aims at the implementation of unstable cavity operation for both resonators to achieve good beam quality at both laser wavelengths (i.e., λ2 and λ3). The reflectivity of this output coupler is designed to obtain optimized high energy at λ2 and λ3. Mirror M3 and a dichroic mirror, DM1 are used to direct and combine the oscillating beam at λ2 with the second oscillating beam at λ3 within the coupled cavity. The dichroic mirror DM1 is configured to highly reflect light at λ2 and highly transmit light at λ3. The combined output lasers are collimated with a lens L6 before entering the frequency conversion module. It should be noted that in the example shown in FIG. 7, the two laser mediums (i.e., LM1 and LM2) are birefringent in nature so that the laser output will be naturally polarized. The tuning of polarization for each beam generated from each resonator can be realized by rotating the laser medium LM1 or LM2. In the case of an isotropic laser medium used, a polarizing element should be inserted into the resonator to generate a linear polarized beam.

Configuration C: Two Laser Cavities Sharing One Common High Reflector to Form Cavities.

In another embodiment, the two laser cavities share one common high reflector, HR. FIG. 8 illustrates this configuration in which two resonators comprise birefringent laser medium. Similar to Configuration A, each new laser beam coming out of its corresponding resonator has its dedicated collimating lens (i.e., L4 or L5) for laser beam collimating and half waveplate (i.e., HWP1 or HWP2) for rotating its polarization to optimize the nonlinear frequency conversion in the next module. Related to using one common HR, two additional dichroic mirrors (i.e., DM2 and DM3) are needed not only for forming two laser resonators but also for introducing pump beams to the corresponding resonators. DM2 is used to highly reflect laser beam at λ2 and highly transmit pump laser. DM3 has coatings that are highly reflective at λ3 and highly transmissive at pump wavelength. The two beams at λ2 and λ3 follow the same beam path after DM1.

Configuration D: Two Laser Cavities Sharing The Same Cavity Mirrors

This is a combined version of Configurations B and C. The same HR mirror and output coupler, OC are used to form two coupled laser resonators to achieve more compact design and easier alignment. HR mirror has high reflective coating for two laser wavelengths λ2 and λ3. The functionality of this configuration is almost identical to that of Configuration B except for the same HR used. FIG. 9 shows an example of this configuration with two laser rods being anisotropic.

Configuration E: Two Laser Cavities Formed with Two Separate Monolithic Rods

In some examples, the two laser resonators can be configured as monolithic arrangement, in which each laser cavity is formed by a laser rod itself as shown in FIG. 10. In this case, the coatings on the front end and exit end for each rod act as high reflector and output coupler to form laser resonator. For the laser rod, LM1, its entrance surface, S1 will have coatings to be highly reflective at laser wavelength, λ2 and highly transmissive at pump wavelength λ1 to implement the function of a HR mirror. The output end of LM1, i.e., S2 will have concave curvature intending to achieve unstable cavity operation to obtain good beam quality at high energy. This concave surface also has partially reflective coatings for coupling the laser out of the cavity. Likewise, laser rod LM2 forms monolithic cavity II with coatings on its input end S1 and output end S2 acting as cavity high reflector and output coupler respectively. The parallelism between two surfaces of each rod (i.e., S1 and S2) should be within 5 arc seconds to ensure the proper laser oscillation. Such a monolithic approach offers some benefits including compact design and no need for resonator alignment. It should be noted that this configuration can only be applied to laser medium which can give linearly polarized output required for frequency conversion because there is no way to add any polarizing element within the cavity.

Configuration F: Two Laser Cavities Formed With One Composite Monolithic Rod

In one embodiment, the cavity may be further simplified by fabricating a composite monolithic rod. As shown in FIG. 11, such an integrated rod consists of two sections, in which each one is a monolithic laser to generate one laser wavelength (i.e., λ2 or λ3). The interface of two sections has a highly reflective coating for dual wavelengths of λ2 and λ3 to act as a common HR mirror for each monolithic resonator. The two surfaces of the composite rod have concave curvatures with specific coatings to act as output couplers forming two monolithic resonators with their common HR coating sandwiched in between two sections. Specifically, one surface end (i.e., S1) has coating which can partially reflect laser at the wavelength λ2 and highly transmit the pump laser while the other surface, S2 is coated with the coatings which can be partially reflective at λ3 and highly transmitting at the pump laser wavelength (i.e., λ1). The parallelism between HR interface and S1 or HR interface and S2 should be within 5 arc second to ensure proper laser operation. The fabrication of such composite monolithic rod may be through optical bonding or diffusion bonding. The material of each section can be the same kind or different types. In case of different kinds of laser host medium are used, the optical contact is a preferrable way for forming a monolithic composite rod. Similar to Configuration E, the laser medium used to form this composite rod should be naturally anisotropic necessary to produce linearly polarized lasers.

Use of such a composite monolithic rod (i.e., LM) involves introducing pump lasers from each end of the rod, as shown in FIG. 12. One arm of the pump beam passes through a focusing lens (i.e., L2) and a dichroic mirror, DM2 and then is focused into the first section of the composite rod to generate laser at λ2. The output of this laser beam is reflected by DM2 and mirrors, M5 and M3 before it is combined with the second generated laser at λ3 via a dichroic mirror DM1. Similar to the previous configurations, L4 is placed to collimate the first laser. A half waveplate, HWP1 is used to tune the polarization of output beam (i.e., λ2) for later frequency conversion. The pump of the second section (or Cavity II) is implemented with two mirrors (i.e., M2 and M4), a focusing lens, L3, and a dichroic mirror, DM4. The dichroic mirror DM4 can highly reflect pump beam and highly transmit the laser beam generated from Cavity II (i.e., the second section of the monolithic composite rod). A lens L5 and a half waveplate HWP2 are used to collimate and adjust polarization of the generated new laser at λ3, respectively.

The Frequency Conversion Module

The frequency conversion module can receive the laser beams from the dual laser module with three modes (i.e., single wavelength λ2 or λ3, or combined two wavelengths) (see FIG. 2). It can also receive a laser beam at pump wavelength of λ1, which is one of the outputs of the pump laser module. FIGS. 13 and 15 show two typical examples of this module. It has at least two functionalities. The first one is to selectively deliver the four near infrared lasers to the handpiece module. These four near infrared lasers include one laser beam at λ1 (i.e., 700-980 nm) and three laser beams generated from the dual laser module at λ2 (i.e., ~1 μm), λ3 (i.e., ~1.3 μm), or mixed λ2 & λ3. As another function, it can implement the nonlinear frequency conversion through at least one non-linear optical crystal to generate three new wavelengths in the visible range. These are green laser at λ4 (i.e., 515-540 nm) which is the frequency doubled λ2 (i.e., ~1.03-1.08 μm), red laser at λ5 (i.e., 650-675 nm), which is the frequency doubled λ3 (i.e., 1.3-1.35 μm), and yellow/orange laser at λ6 (i.e., ~580-600 nm) which is the sum frequency of λ2 and λ3. Altogether, this module is capable to deliver six individual wavelengths, λ1-6 (i.e., 700-980 nm, 1.03-1.08 μm, 1.3-1.35 μm, 515-540 nm, 650-670 nm, and 580-600 nm). It can also be configured to deliver a laser beam with mixed wavelengths of two infrared lasers (i.e., λ2 and λ3).

The implementation of nonlinear frequency conversion can be realized by using at least one crystal. In one embodiment, a single crystal can be employed for producing all three visible wavelengths via second generation ($\lambda 4 = \lambda 2/2$ and $\lambda 5 = \lambda 3/2$) and sum frequency generation ($\lambda 6 = \lambda 2 * \lambda 3/(\lambda 2 + \lambda 3)$). In another embodiment, more than one nonlinear crystal is used for frequency conversion.

One Nonlinear Crystal for Generating all Three Visible Wavelengths Via Frequency Conversion In this case, the phase match condition can be satisfied by either critical phase matching or non-critical phase matching. It is preferred to introduce a noncritical phase match method, in which different nonlinear frequency generation can be achieved by tunning the temperature of the crystal without adjusting crystal's orientations. FIG. 13 shows a typical example for this approach. In this configuration, the pump beam directly from the pump laser module will be directed to a handpiece as a final output wavelength of λ1

(i.e., 700-980 nm) with an energy up to 60 J and peak power of ~20 kW. The second input of this module is one of the three laser beams of two wavelengths (λ2, λ3, or mixed λ2 with λ3). A removable mirror, MM2 can selectively send one of these three incoming beams either to the handpiece as another output (i.e., λ2, λ3, or mixed λ2 with λ3) or to an arm consisting of a nonlinear crystal for frequency conversion. The removable mirror, MM2 can be a flipping mirror, or a mirror mounted on a translation/rotation stage. It will have coatings which can be highly reflective at two near infrared laser wavelengths (i.e., λ2 and λ3). Based on the different laser configurations produced from the pump laser module and the dual laser module, this current module can selectively deliver seven laser beams with six different wavelengths, which are described as follows.

Pump Laser Beam (i.e., λ1) as a Final Output

The unique configuration of this application allows the system to deliver the pump laser directly to the handpiece as a final output. The capability of delivery of long pulsed (i.e., μs to ms) laser at the wavelength of 700-980 nm will enable the treatment of unwanted hair as well as vascular lesions and pigmentation for darker skin. This output mode will be activated when the moving mirror, MM1 in pump laser module is positioned in the pump beam path, as shown in FIG. 3. The delivery of the pump laser to the handpiece is implemented by a mirror, M8 and a moving mirror, MM3, which can be a flipping mirror, or a mirror mounted on a translation or rotation stage (See FIG. 14A). Both M8 and MM3 will have a coating which can be highly reflective at the pump laser wavelength (i.e., λ1).

One of Laser Beams of Near Infrared Wavelength (λ2, λ3, or Mixed λ2 with λ3) Generated from the Dual Laser Module as an Output This configuration is enabled when the moving mirror, MM1 in the pump laser module is moved out of the pump beam path (see FIG. 3). As mentioned in the previous section, the three laser beams of two wavelengths (i.e., λ2 and λ3) can be selectively generated from the dual laser module when the pump laser is delivered to that module. As shown in FIG. 14B, if one of these three near infrared laser beams (λ2, λ3, or mixed λ2 with λ3) is delivered to the frequency conversion module, it will be directed selectively to one of the two arms with a movable mirror, MM2, which highly reflects laser at wavelengths of both λ2 and λ3. When MM2 is positioned in the input beam path, the input beam at a wavelength of λ2, λ3, or mixed λ2 and λ3 will be directed to the handpiece as an output laser beam via mirrors, M6, M7, and DM5. M6 and M7 have coatings that can highly reflect laser at both λ2 and λ3. In one example, DM5 may be a dichroic mirror, which has coatings to be highly reflective at two near infrared wavelengths (i.e., λ2 and λ3) and highly transmissive at three visible wavelengths (i.e., 515-540 μm, 650-670 nm, and 580-600 nm). In an alternative example, DM5 may be a movable mirror coated with the highly reflective coating at both wavelengths (i.e., λ2 and λ3). In this case, the delivery of one of the three near infrared laser beams will be made possible with DM5 positioned into the beam path. After it gets reflected by DM5, this fundamental near infrared laser beam will propagate to the handpiece coincidently with the three visible laser beams obtained from nonlinear frequency conversion processes, which will be described in the next section.

The Visible Laser Beams Generated Via Nonlinear Frequency Conversion As Outputs

When MM2 is moved out of the input beam path, the input laser beam at a wavelength of λ2, λ3, or mixed λ2 and λ3 is focused into a nonlinear crystal, NLC with a focusing lens, L7 for frequency conversion to generate a new wavelength (i.e., λ4 (=λ2/2), 25 (=λ3/2), or λ6 (=λ2*λ3/(λ2+λ3)), as shown in FIG. 14C. Specifically, λ4 and λ5 are generated by the second harmonic frequency conversion of the fundamental wavelength of λ2 and λ3, respectively. They fall into the ranges of green wavelength (i.e., λ4=515-540 μm) and red wavelength (i.e., λ5=650-670 nm), respectively. 26 is in yellow orange wavelength range (i.e., 580-600 nm) and obtained by sum frequency conversion of two fundamental wavelengths of λ2 and λ3. All these three nonlinear frequency conversion processes can be implemented with a common nonlinear crystal, NLC. Lens L8 is placed right after NLC to collimate the laser beam at λ4, λ5, or λ6. A dichroic mirror, DM6 will reflect the residual unconverted laser at λ2, λ3, or mixed λ2 and λ3 and send it to a beam dump while the converted new laser beam passes through it before it further propagates through the mirror, DM5. As described in the last section, DM5 is designed to be functional for multiple wavelengths in case that it is a dichroic mirror. In another embodiment, DM5 can be a removable mirror. The generated visible wavelength will propagate forward following the same beam path as one of the near infrared fundamental lasers (i.e., λ1, λ2, λ3, or mixed λ2 and λ3) with MM3 out of the beam path.

In summary, with the three selectable operation modes delivered by dual laser module and selectable pump laser output as two inputs, this disclosed module is capable of producing seven laser beams with six single wavelengths (i.e., λ1-6) and one mixed wavelength (i.e., λ2 and λ3). The optical layout is such designed that all these seven laser beams will propagate coincidently into the handpiece for final beam delivery. In one example, pump laser is 60 J Alexandrite laser with a peak power of ≥20 kW at 753 nm. With two laser cavities containing $Nd^{3+}$ doped laser crystals (i.e., Nd:YAG for 1.064 μm and Nd:YAP for 1.342 μm), the disclosed device is able to deliver joule level output for all the wavelengths (e.g., 60 J @753 nm, ~30 J @1.064 μm, ~24 J@1.342 μm, ≥5 J@532 nm, ≥5 J@671 nm, ≥5 J @593 nm, and >25 J @blended wavelengths of 1.064 μm and 1.342 μm.

The disclosed apparatus can include a single nonlinear laser crystal, NLC. This crystal is used for both second harmonic generation (SHG) of each of the laser wavelengths generated from dual laser module (λ2 or λ3) and sum frequency generation (SFG) of those two (i.e., λ2 and λ3). In one embodiment, such nonlinear frequency conversion will be implemented with non-critical phase matching, which can be achieved by tunning the crystal temperature. In a preferred example, this crystal is lithium triborate (LBO). It is possible to adjust the LBO temperature to 275K, 4λ2K and 307K to achieve type I noncritical phase matching (i.e., O+O→E) for SHG of 1.064 nm from Nd:YAG laser emission, SHG of 1.342 nm from Nd:YAP emission and SFG of two, respectively. The crystal will be housed in a temperature oven for temperature stabilization and tuning.

In terms of sum frequency generation, several laser materials can be used to generate ~1 μm and ~1.3 μm lasers as fundamental input beams. Table 2 lists some examples to show the generation of yellow orang wavelengths via SFG processes.

TABLE 2 examples of yellow orange wavelength generation with sum frequency generation of two laser emission lines.

| λ2, μm | λ3, μm 1.313 (Nd:YLF (σ)) | 1.319 (Nd:YAG) | 1.321 (Nd:YLF (π)) | 1.329 (Nd:CNGG) | 1.338 (Nd:YAB[9]) | 1.339 (b-cut Nd:YAP(a-axis)[14] | 1.341 (b-cut Nd:YAP(c-axis)[14] | 1.342 ($Nd:YVO_4$)[7]) |
|---|---|---|---|---|---|---|---|---|
| 1.030 (Yb:YAG[10]) | 0.577 | 0.578 | 0.579 | 0.580 | 0.582 | 0.582 | 0.583 | 0.583 |
| 1.047 (Nd:YLF (π)) | 0.583 | 0.584 | 0.584 | 0.586 | 0.587 | 0.588 | 0.588 | 0.588 |
| 1.053 (Nd:YLF (σ)) | 0.584 | 0.586 | 0.586 | 0.588 | 0.589 | 0.589 | 0.590 | 0.590 |
| 1.062 (Nd:YAB[9]) | 0.587 | 0.588 | 0.589 | 0.590 | 0.592 | 0.592 | 0.593 | 0.593 |
| 1.063 ($Nd:GdVO_4$[8] | 0.587 | 0.589 | 0.589 | 0.591 | 0.592 | 0.593 | 0.593 | 0.593 |
| 1.064 (Nd:YAG, $Nd:YVO_4$[7], b-cut Nd:YAP(a-axis) [14] | 0.588 | 0.589 | 0.589 | 0.591 | 0.593 | 0.593 | 0.593 | 0.593 |
| 1.079 (b-cut Nd:YAP (c-axis)[14]: | 0.592 | 0.593 | 0.594 | 0.596 | 0.597 | 0.598 | 0.598 | 0.598 |

Nd:CBGG: neodymium-doped calcium-niobium-gallium-garnet
$Nd:GdVO_4$: Neodymium-doped gadolinium orthovanadate
Nd:YAB: Neodymium-doped Yttrium aluminum borate More than One Crystal Used for Generating Three Visible Wavelengths Via Frequency Conversion In an alternative embodiment, more than one nonlinear crystal can be used for frequency conversion processes including second harmonic generations of two fundamental wavelength, λ2 and λ3, and sum frequency of them. FIG. 15 depicts an example of the optical layout for frequency conversion module with three crystals (i.e., NLC1, NLC2, and NLC3) with each for one dedicated nonlinear frequency conversion. The selective beam delivery of pump wavelength and directing three input laser beams for corresponding frequency conversions are implemented with three moving mirrors including MM3, MM4, and MM5. Both MM3 and MM4 have coatings which can be highly reflective at two fundamental wavelengths generated from dual laser module (i.e., λ2 and λ2) while MM5 has a coating to highly reflect pump laser beam at λ1. In this configuration, there are four optical arms for four different functionalities, which can be described as follows.

Pump Laser Beam (i.e., λ1) As A Final Output

This output mode will be enabled when the moving mirror, MM1 in pump laser module is positioned in the pump beam path, as shown in FIG. 3. When the pump beam enters the frequency conversion module, it will be further directed to the handpiece via M8, DM7, and a moving mirror, MM5 (see FIG. 16A). DM7 is a dichroic mirror, which is highly transmissive at all three near infrared wavelengths (i.e., λ1-3) and highly reflective at the sum frequency of λ2 and λ3 (i.e., λ6). There are several clinical benefits of the availability of the pump wavelength (i.e., 700-980 nm) at a pulse duration ranging from a few hundred microseconds to a few hundred milliseconds including various treatments of unwanted hair as well as vascular lesions and pigmentation for darker skin.

One of Laser Beams of Near Infrared Wavelength (λ2, λ3, or Blended λ2 with λ3) Generated from the Dual Laser Module as an Output This configuration is enabled when the moving mirror, MM1 in the pump laser module is moved out of the pump beam path (see FIG. 3). As mentioned earlier, the three laser beams of two wavelengths can be selectively generated from the dual laser module.

As shown in FIG. 16B, if one of the three near infrared laser beams (λ2, λ3, or mixed λ2 with λ3) is delivered to the frequency conversion module, it will be directed selectively to one of the four laser beam arms with a set of two movable mirrors, MM3 and MM4, which highly reflects laser at wavelengths of both λ2 and λ3. This beam delivery mode will be activated when both MM3 and MM4 are moved out of the beam path. In this case, the incoming one of the three fundamental laser beams at a wavelength of λ2, λ3, or mixed λ2 and λ3 will pass through a dichroic mirror, DM10 as an output of this frequency conversion module (or an input of the handpiece). Dichroic mirror DM10 will have multi-functional coatings which is capable to highly transmit laser at two fundamental wavelengths of λ2 and λ3 and highly reflect two visible wavelengths generated from second harmonic conversion of λ2 and λ3 (i.e., λ4 and λ5). The use of DM10 can ensure that these two visible laser beams can propagate to the handpiece coincidently with the fundamental laser beams at λ2, λ3, and mixed λ2 and λ3.

Green/Red Laser Beam as an Output

This beam delivery mode will be enabled when the moving mirror, MM3 is positioned to be out of the incoming beam path (FIG. 16C) while another moving mirror immediately after it (i.e., MM4) is in the beam path. In case of the fundamental laser beam at a wavelength of λ2 being selected, it will be directed into an optical arm which comprises of a nonlinear optical crystal, NLC1 for frequency doubling of fundamental laser wavelength of λ2 via reflections off from MM4 and a dichroic mirror, DM8. The dichroic mirror, DM8 has coatings which can highly reflect laser at λ2 and highly transmit laser at the other fundamental wavelength (i.e., λ3). This optical arm further consists of a pair of lenses, L11 for focusing the fundamental laser beam at λ2 and L12 for collimating the newly generated green laser via SHG (i.e., λ4). In one embodiment, λ4 is in the range of 515 to 540 nm. This green laser beam at λ4 can be further delivered to the handpiece following the same beam path as the fundamental laser beams (i.e., λ2, λ3, or mixed λ2 and λ3) through the reflection by a dichroic beam DM9 and DM10. Dichroic mirror, DM9 can highly reflect green laser beam at λ4 while highly transmitting lasers at an infrared wavelength of λ2 and red wavelength of λ5. The unconverted fundamental laser at λ2 will pass through DM9 and gets recycled by a beam dump.

In case of the other fundamental wavelength (i.e., λ3) is selected, it will pass through DM8 and be sent to another optical arm consisting of a second nonlinear optical crystal (i.e., NLC2) by M9, which is highly reflective at λ3. NLC2 is used for second harmonic frequency conversion of λ3 to generate red laser wavelength λ5 ranging from 650 nm to 670 nm. The combination of three mirrors (i.e., DM11, DM9 and DM10) will direct the newly generated red laser at λ5 to the next module (i.e., handpiece), which is collinear with the green laser (i.e., λ4) and all the near infrared laser beams (i.e., λ1-3, and mixed λ2 and λ3). Dichroic mirror DM11 is coated with coatings which can highly reflect red laser beam at λ5 and highly transmit unconverted fundamental laser at λ3. L13 and L14 are used to focus the fundamental laser beam at λ3 into NLC2 and collimate the converted red beam, respectively.

Yellow/Orange Laser Beam as an Output

This mode is activated when the laser with blended dual fundamental wavelengths is selected from the dual laser module. As shown in FIG. 16D, the blended laser beam is sent to an optical arm comprising a third nonlinear optical crystal, NLC3 for sum frequency conversion to generate yellow orange laser by the reflections from the moving mirror MM3 and M6. Similar to the other two arms for nonlinear frequency conversion, a set of lenses (i.e., L9 and L10) are placed before and after NLC3 for focusing incoming the blended wavelengths of λ2 and λ3 into the crystal and collimating the converted yellow/orange laser at λ6 (i.e., 580-600 nm), respectively. The collimated yellow/orange laser is further delivered to the next module (i.e., handpiece) by the dichroic mirror, DM7 and the moving mirror, MM5. The functionality of DM7 and MM5 is described in section (a). The two unconverted mixed wavelengths (i.e., λ2 and λ3) can be stopped by a beam dump. It should be mentioned that all the laser beams delivered by this module will propagate to the next module coincidently.

The selection of the nonlinear crystal should consider at least three factors including high second order nonlinearity, sufficient transparency at the wavelengths of interest, easy implementation of phase matching, as well as reasonable costs. In some examples, these crystals can be LBO, KTP, KDP, BBO, etc. Both the noncritical phase matching and critical phase matching can be employed for frequency conversion depending on crystal properties as well as design preferences.

The Handpiece

The handpiece module receives the output from the frequency conversion module, which may include six laser wavelengths and seven laser beam modes. In one example, the handpiece comprises at least one lens system, which can deliver at least one laser beam to the treatment site (i.e., skin) with a full beam of different spot sizes. This is so called zoom handpiece. One or multiple handpieces may be involved. In the case where one common handpiece is used for all the wavelengths, it should be operational for all the delivered laser beams. More specifically, the optical coatings on the optics within the handpiece should work for all the wavelengths. In some alternative embodiments, more than one handpiece may be used. In this case, some of the laser beam delivery will share the same handpiece. Typically, the laser beams for treating vascular lesions, pigmentation, and unwanted hair may involve using a zoom handpiece to produce laser beam of specific spot size at visible wavelengths (i.e., λ4-6) or two infrared wavelengths (i.e., λ1 and λ2).

In some other examples, the laser beams from the frequency conversion module can be delivered to skin with an array of many microbeams. This is so called fractional treatment. This treatment is intended to create microinjuries in skin while sparing the untreated area. The fractionated treatment has been proved to be safer compared to the treatment with full beam in terms of low-down time and less complications. For fractional skin treatment, at least one of the near infrared wavelengths generated by this apparatus (i.e., ~1.3 μm) is useful. At this wavelength, laser can penetrate to dermis thanks to minimal melanin absorption, and create microinjuries in that skin layer due to sufficient water absorption. The heating of collagen may stimulate the shrink of collagen leading to skin tightening or stimulate collage growth by triggering a healing response in the skin, which may be caused by induced non-ablative microthermal damage. To generate a microbeam pattern, at least one beam splitting element will be needed. In one example, it may be a refractive lens array. In another example, it may be a combination of diffractive beam splitter and a lens.

In an alternative embodiment, two or more laser pulses of different wavelengths can be delivered in sequence or simultaneously. This feature may be useful for skin rejuvenation treatment with two near infrared lasers (i.e., ~1 μm (λ2) and ~1.3 μm (λ3). As described in the dual laser module section, the delivery of two laser beams at ~1 μm and ~1.3 μm in different modes can be enabled by the pump beam steering assembly, PSA, as shown FIGS. 4-5. If two laser pulses at different wavelengths (i.e., λ2 and λ3) is selected to be delivered in sequence, the delay time between two pulses is determined by the switching time between two stops of PSA (i.e., stops A and B) in a configuration shown in FIG. 5 or by the switching time between two orientations of the half waveplate for S and P polarization in another configuration of PSA shown in FIG. 6. FIG. 17A illustrates the delivery of two laser pulses of two wavelengths in sequence. The delivery of two laser pulses at two different wavelengths of λ2 and λ3 simultaneously can be realized by positioning the PSA at Step (C) shown in FIG. 5 or by positioning the half waveplate to produce a polarization at 45-degree relative to S or P polarization as shown in FIG. 6. FIG. 17B shows the two pulses at λ2 and λ3 delivered concurrently. It should be mentioned that the energy for two laser pulses may be the same or different depending on specific treatment requirements. The output energy control may be implemented by varying the pulse energy delivered to each laser resonator shown in FIGS. 4, 7-10, and 12. In another example, the variation of the energy of each laser pulse may be realized by introducing laser energy attenuator presented in a handpiece for each laser.

In terms of the beam profile characteristics for the delivered laser beams with blended wavelengths, the laser beams of the blender wavelengths may be configured as two overlapping solid beams or as mixed beam profiles. For the latter case, in one embodiment, the laser at λ2 (i.e., ~1 μm)

can be delivered to the treatment site (i.e., skin) in a form of a solid beam while the other laser at λ3 (i.e., ~1.3 μm) can be split into multiple microbeams and used to generate microbeam array on the skin for fractionated treatment, as shown in FIG. 18. The introduction of mixed beam profiles for the two wavelengths may offer some clinical benefits. The single solid beam at ~1 μm may be able to penetrate across epidermis to heat the dermis while the fractionated microbeams at the other longer wavelength (i.e., ~1.3 μm) may implement the nonablative fractional treatment to create microinjuries within dermis. The combination of localized bulk heating caused by ~1 μm laser and microinjury created by ~1.3 μm may bring in more effective collagen regrowth compared to individual treatment for each beam mode and wavelength. The implementation of such blended beam profiles delivered to skin may involve further beam separation of two wavelengths followed by beam conditioning and beam recombining.

In one preferred embodiment, a dedicated handpiece may be designed to achieve this functionality. FIG. 19 shows two examples of the handpieces that can deliver the above-mentioned blended beam profiles. These two handpieces will receive the laser beams of mixed two wavelengths (i.e., ~1 μm and ~1.3 μm). The collinear laser beams can be separated by a dichroic mirror, DM8, which is coated to be capable of highly reflecting shorter wavelength (i.e., ~1 μm) and highly transmitting the other wavelength (i.e., ~1.3 μm). The reflected ~1 μm laser beam is then directed by mirrors, M12 and M13 to a dichroic mirror DM9. DM9 can combine the reflected ~1 μm laser with the transmitted ~1.3 μm laser and direct combined beams to the treatment site. An energy attenuator, A1 is used to regulate the delivered energy at ~1 μm. The transmitted laser beam at ~1.3 μm through DM8 can be split into multiple microbeams with a lens array LA (see FIG. 18(*a*)) or a diffractive beam splitter, DBS (FIG. 18(*b*)). Another energy attenuator, A2 is used to control the energy for this wavelength (i.e., ~1.3 μm). DM9 functions the same as DM8. For the configuration with a diffractive beam splitter, a lens, L15 will be used to produce the desirable microbeam spot size on the skin. As a result, the final output of these handpieces will be a single solid beam at ~1 μm superimposed with an array of many microbeams at ~1.3 μm.

In terms of the capability of the laser wavelength generation, this disclosed device can deliver six individual wavelengths (i.e., 700-980 nm, 1.03-1.08 μm, 1.3-1.35 μm, 515-540 nm, 650-670 nm, and 580-600 nm). It can also be configured to deliver a laser beam with mixed wavelengths of two infrared lasers (i.e., ~1 μm and ~1.3 μm).

The disclosures shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the examples described above may be modified within the scope of the appended claims.

One preferred apparatus is a long-pulsed Joule level solid state laser system which can selectively deliver the lasers of wavelengths from green, orange, red and near infrared for customized treatment of vascular lesions, unwanted hair removal, pigmented lesions, and skin rejuvenation. It may replace a flashlamp pumped liquid dye laser and is expected to deliver a similar energy or peak power but with much better reliability and consistency. Furthermore, the capability of generation of green wavelength (e.g., 524 nm or 532 nm), orange wavelength (e.g., 593 nm), and near infrared wavelength (e.g., 1064 nm) will empower the customized treatment of blood vessels of different sizes and different depths. 755 nm laser may also be used for hair removal or pigmented lesions. In addition, addition of two near infrared wavelengths (i.e., ~1 μm and ~1.3 μm) may expand the treatment scope to skin tightening. Therefore, such a high energy laser device with switchable multi-wavelength capability and multiple beam profiles may have more clinical applications than the current system leading to having better market penetration.

In addition, the disclosed device can also help to better position and compete with several solid-state vascular lasers on the market by offering multiple wavelengths and higher energy for versatile and more effective treatments.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

What is claimed is:

1. A multiple frequency laser system for treating skin conditions comprising:

a handpiece for treating skin conditions;

a pump laser module having a single laser beam at a first frequency;

a dual laser module receiving the laser beam at the first frequency and including dual free running laser resonators to produce a laser beam at a second frequency and a laser beam at a third frequency;

a frequency conversion module receiving as inputs the laser beam at the second frequency and the laser beam at the third frequency and configured to selectively provide laser beams to the handpiece including a second harmonic generation of the second frequency, a second harmonic generation of the third frequency, a summed frequency generation of the second frequency and the third frequency, the laser beam at the first frequency, the laser beam at the second frequency, and/or the laser beam at the first frequency combined with the laser beam at the second frequency; and the handpiece receiving the laser beams from the frequency conversion module and delivering them to skin for treatment with solid beam of variable size, a fractional microbeam pattern, or a hybrid beam pattern of a solid beam and fractional microbeams.

2. The system of claim 1 further including a first optical subsystem for directly providing the laser output at the first frequency output by the pump laser to the handpiece for delivery to a patient's skin.

3. The system of claim 1 further including a second optical subsystem for directly providing the laser output at the second frequency, the laser output at the third frequency, and the laser output at the mixed second and third frequencies from the dual laser module to the handpiece for delivery to a patient's skin.

4. The system of claim 1 in which the pump laser module includes a free running long pulsed high energy laser.

5. The system of claim 1 in which the dual laser resonators include laser mediums of different kinds or same types.

6. The system of claim 1 in which each of the laser resonators is a free running laser pumped simultaneously by the pump laser module.

7. The system of claim 1 in which each of the dual laser resonators is configured as unstable cavity to achieve both high energy and good beam quality for efficient nonlinear frequency conversion.

8. The system of claim 1 in which each of the dual laser resonators contain rare earth ions doped crystals or ceramics as laser gain medium.

9. The system of claim 1 in which the frequency conversion module is implemented in an extracavity configuration.

10. The system of claim 1 in which the frequency conversion module includes at least one non-linear optical crystal.

11. The system of claim 1 in which the first frequency is approximately 700-980 nm, the second frequency is approximately 1.03-1.08 μm, and the third frequency is approximately 1.3-1.35 μm.

12. The system of claim 1 in which the laser output at the second harmonic frequency of second frequency is approximately 515-540 nm and the laser output at the second harmonic frequency of the third frequency is approximately 650-675 nm.

13. The system of claim 1 in which the sum frequency of the second frequency and the third frequency produces a laser beam at a frequency of approximately 580-600 nm.

14. The system of claim 1 in which the laser beam of mixed second frequency and third frequency can be deliver to the skin with a pre-determined delay or simultaneously.

15. The system of claim 1 in which the laser system delivers blended beam patterns for the second frequency and the third frequency.

16. The system of claim 1 in which the laser system delivers variable pulse durations ranging from a few hundred microseconds to hundreds of milliseconds controlled by tunning the pulse duration of pump laser.

17. A multiple frequency laser method for treating skin conditions, the method comprising:

providing a laser beam at a first frequency;

producing, from the laser beam at the first frequency, a laser beam at a second frequency and a laser beam at a third frequency; and receiving the laser beam at the second frequency and the laser beam at the third frequency and selectively providing laser beams to a handpiece including a second harmonic generation of the second frequency, a second harmonic generation of the third frequency, sum frequency generation of the second frequency and the third frequency, the laser beam at the first frequency, the laser beam at the second frequency, and/or the laser beam at the first frequency combined with the laser beam at the second frequency.

18. The method of claim 17 further including directly providing the laser beam at the first frequency to the handpiece for delivery to a patient's skin.

19. The method of claim 17 further including directly providing the laser beam at the second frequency, the laser beam at the third frequency, and the laser beam at the mixed second and third frequencies to a handpiece for delivery to a patient's skin.

20. The method of claim 17 in which the laser beam at the first frequency is produced by a free running long pulsed high energy laser.

21. The method of claim 17 in which dual laser resonators are used to produce the laser beam at the first frequency, the laser beam at the second frequency, and the laser beam at the third frequency.

22. The method of claim 21 in which each of the laser resonators is a free running laser pumped simultaneously by a pump laser.

23. The method of claim 21 in which each of the dual laser resonators is configured as unstable cavity to achieve both high energy and good beam quality for efficient nonlinear frequency conversion.

24. The method of claim 21 in which each of the dual laser resonators contains rare earth ions doped crystals or ceramics as laser gain medium.

25. The method of claim 17 in which the frequency conversion is implemented in an extracavity configuration.

26. The method of claim 17 in which the first frequency is approximately 700-980 nm, the second frequency is approximately 1.03-1.08 μm, and the third frequency is approximately 1.3-1.35 μm.

27. The method of claim 17 in which the laser output at the second harmonic frequency of second frequency is approximately 515-540 nm and the laser output at the second harmonic frequency of the third frequency is approximately 650-675 nm.

28. The method of claim 17 in which the sum frequency of the second frequency and the third frequency produces a laser beam at a frequency of approximately 580-600 nm.

29. The method of claim 17 in which the laser beam of mixed second frequency and third frequency is delivered to the skin with a pre-determined delay or simultaneously.

30. The method of claim 17 including producing blended beam patterns for the second frequency and the third frequency.

31. The method of claim 17 including delivering variable pulse durations ranging from a few hundred microseconds to hundreds of milliseconds.

* * * * *